US012625137B2

(12) United States Patent
Gundavarapu et al.

(10) Patent No.: US 12,625,137 B2
(45) Date of Patent: May 12, 2026

(54) PHOTONIC BIOSENSORS FOR MULTIPLEXED DIAGNOSTICS AND A METHOD OF USE

(71) Applicant: SiPhox, Inc., Burlington, MA (US)

(72) Inventors: Sarat Gundavarapu, Cambridge, MA (US); Ebrahim Al Johani, Somerville, MA (US); Diedrik Rene Vermeulen, Arlington, MA (US)

( * ) Notice: Subject to any disclaimer, the term of this patent is extended or adjusted under 35 U.S.C. 154(b) by 29 days.

(21) Appl. No.: 18/126,014

(22) Filed: Mar. 24, 2023

(65) Prior Publication Data

US 2024/0094204 A1 Mar. 21, 2024

Related U.S. Application Data

(60) Provisional application No. 63/302,385, filed on Jan. 24, 2022.

(51) Int. Cl.
*G01N 33/569* (2006.01)
*B01L 3/00* (2006.01)
*G01N 33/543* (2006.01)

(52) U.S. Cl.
CPC .. *G01N 33/56983* (2013.01); *B01L 3/502715* (2013.01); *G01N 33/54373* (2013.01); *B01L 2200/04* (2013.01); *B01L 2200/18* (2013.01); *B01L 2300/0636* (2013.01); *B01L 2300/0816* (2013.01); *G01N 2333/165* (2013.01); *G01N 2469/10* (2013.01)

(58) Field of Classification Search
CPC ............ B01L 2200/04; B01L 2200/18; B01L 2300/0636; B01L 2300/0816; G01N 2333/165; G01N 2469/10
See application file for complete search history.

(56) References Cited

U.S. PATENT DOCUMENTS

2006/0170931 A1* 8/2006 Guo .................. G01N 21/7746
356/480
2016/0231274 A1* 8/2016 Tirapu Azpiroz .. B01L 3/50273
(Continued)

OTHER PUBLICATIONS

Chen et al., Review of Integrated Optical Biosensors for Point-of-Care Applications, Dec. 18, 2020, p. 1-22, MDPI.
(Continued)

*Primary Examiner* — Maris R Kessel
*Assistant Examiner* — Alea N. Martin
(74) *Attorney, Agent, or Firm* — CALDWELL LLC

(57) ABSTRACT

An apparatus for photonic biosensors for multiplexed diagnostics and a method of use are disclosed. The apparatus includes a portable device configured for point-of-care diagnostics. The portable device includes a photonic sensor chip that includes one or more resonators that is substantially in contact with at least a fluid that includes one or more analytes and the reader device communicatively connected to the photonic sensor chip that includes at least a light source and the reader device is configured to provide an input optical signal using the at least a light source, receive the one or more sensor signals from the photonic sensor chip and determine one or more characteristics of the one or more analytes as a function of the one or more sensor signals and a connecting system, wherein the connecting system is configured to connect the photonic sensor chip and the reader device.

20 Claims, 15 Drawing Sheets

(56) References Cited

U.S. PATENT DOCUMENTS

| | | | |
|---|---|---|---|
| 2017/0067829 A1* | 3/2017 | Duer ................. | G01N 21/6452 |
| 2019/0187162 A1* | 6/2019 | Shastry ............... | G01N 33/487 |
| 2019/0234850 A1* | 8/2019 | Singh ................. | G01N 21/7703 |
| 2020/0011795 A1* | 1/2020 | Schmidt .............. | G01N 21/645 |
| 2021/0069708 A1 | 3/2021 | Govyadinov | |
| 2023/0133866 A1* | 5/2023 | Vermeulen .......... | G02B 6/2938 |
| | | | 435/6.19 |

OTHER PUBLICATIONS

Ramirez et al., Current Trends in Photonic Biosensors: Advances towards Multiplexed Integration, Sep. 30, 2022, p. 1-22, MDPI.

* cited by examiner

200pM Mean Ramp:189.834pm/min

200pM Mean RMSE: 0.013

1000pM Mean RMSE: 0.012

1000pM Mean Ramp:127.882pm/min

20pM Mean Ramp:56.214pm/min

20pM Mean RMSE: 0.007

2pM Mean Ramp:24.061pm/min

2pM Mean RMSE: 0.011

0pM Mean RMSE: 0.003

0pM Mean Ramp:-2.376pm/min

| | |
|---|---|
| 200pM Mean Ramp: 189.834 pm/min | |
| 200pM Mean RMSE: 0.013 | |
| 1000pM Mean Ramp: 127.882 pm/min | |
| 1000pM Mean RMSE: 0.012 | |
| 20pM Mean Ramp: 56.214 pm/min | |
| 20pM Mean RMSE: 0.007 | |
| 2pM Mean Ramp: 24.061 pm/min | |
| 2pM Mean RMSE: 0.011 | |
| 0pM Mean Ramp: -2.376 pm/min | |
| 0pM Mean RMSE: 0.003 | | time (min)

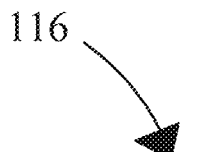
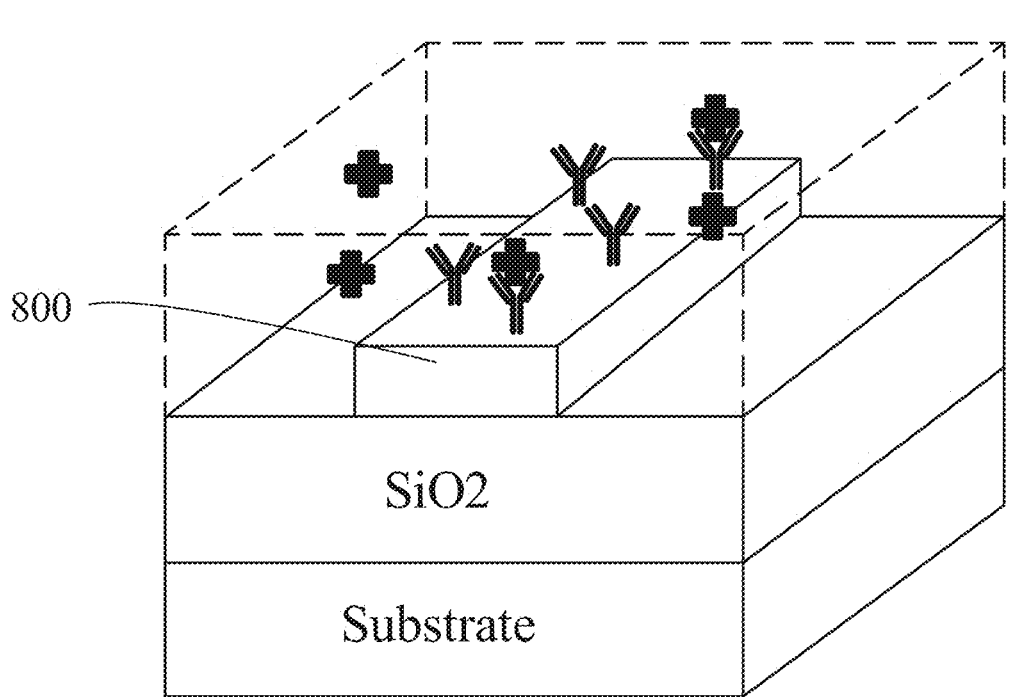
*FIG. 9A*

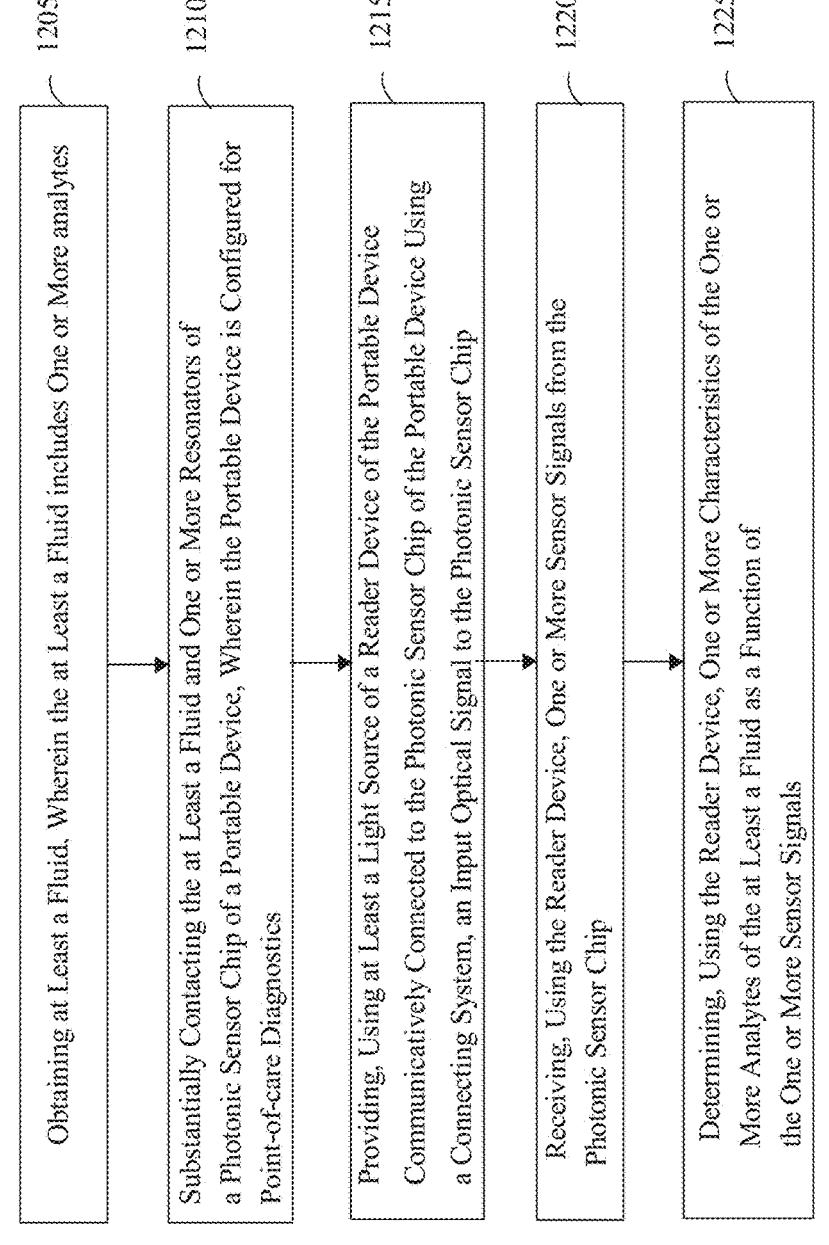

1205

Obtaining at Least a Fluid, Wherein the at Least a Fluid includes One or More analytes

1210

Substantially Contacting the at Least a Fluid and One or More Resonators of a Photonic Sensor Chip of a Portable Device, Wherein the Portable Device is Configured for Point-of-care Diagnostics

1215

Providing, Using at Least a Light Source of a Reader Device of the Portable Device Communicatively Connected to the Photonic Sensor Chip of the Portable Device Using a Connecting System, an Input Optical Signal to the Photonic Sensor Chip

1220

Receiving, Using the Reader Device, One or More Sensor Signals from the Photonic Sensor Chip

1225

Determining, Using the Reader Device, One or More Characteristics of the One or More Analytes of the at Least a Fluid as a Function of the One or More Sensor Signals

PHOTONIC BIOSENSORS FOR MULTIPLEXED DIAGNOSTICS AND A METHOD OF USE

CROSS-REFERENCE TO RELATED APPLICATIONS

This application claims the benefit of priority of U.S. Provisional Patent Application Ser. No. 63/302,385, filed on Jan. 24, 2022, and titled "PHOTONIC BIOSENSORS FOR MULTIPLEXED DIAGNOSTICS," which is incorporated by reference herein in its entirety.

FIELD OF THE INVENTION

The present invention generally relates to the field of biosensors. In particular, the present invention is directed to photonic biosensors for multiplexed diagnostics and a method of use.

BACKGROUND

Biosensors have gained much attention in recent years as a means of detecting analytes. The emergence of personalized medicine, global pandemic risks, and other 21st century health trends has created a demand for low-cost and efficient biosensors capable of monitoring the analytes. Existing techniques for measuring the analytes are generally invasive and/or involve analyzing patient samples using bulky, expensive lab equipment and time consuming, therefore not sufficient.

SUMMARY OF THE DISCLOSURE

In an aspect, an apparatus for photonic biosensors for multiplexed diagnostics is disclosed. The apparatus includes a portable device configured for point-of-care diagnostics, wherein the portable device includes a photonic sensor chip, the photonic sensor chip includes one or more resonators, wherein the one or more resonators is substantially in contact with at least a fluid, wherein the at least a fluid includes one or more analytes and the reader device communicatively connected to the photonic sensor chip, wherein the reader device includes at least a light source and the reader device is configured to provide an input optical signal using the at least a light source, receive the one or more sensor signals from the photonic sensor chip and determine one or more characteristics of the one or more analytes of the at least a fluid as a function of the one or more sensor signals and a connecting system, wherein the connecting system is configured to connect the photonic sensor chip and the reader device.

In another aspect, a method of use of photonic biosensors for multiplexed diagnostics is disclosed. The method includes obtaining at least a fluid, wherein the at least a fluid includes one or more analytes, substantially contacting the at least a fluid and one or more resonators of a photonic sensor chip of a portable device, wherein the portable device is configured for point-of-care diagnostics, providing, using at least a light source of a reader device of the portable device communicatively connected to the photonic sensor chip of the portable device using a connecting system, an input optical signal to the photonic sensor chip, receiving, using the reader device, one or more sensor signals from the photonic sensor chip and determining, using the reader device, one or more characteristics of the one or more analytes of the at least a fluid as a function of the one or more sensor signals.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 7A shows measurements with detailed concentration curve with standard deviations for concentrations of SARS-COV-2 N-protein;

FIG. 9A is an exemplary embodiment of a cross section of a portion of a photonic sensor chip with a silicon nitride ($Si_3N_4$) strip waveguide micro-ring resonator with a binding ligand and analytes;

FIG. 12 is a flow diagram of an exemplary method of use of photonic biosensors for multiplexed diagnostics.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for photonic biosensors for multiplexed diagnostics. The apparatus includes a portable device configured for point-of-care diagnostics, wherein the portable device includes a photonic sensor chip, the photonic sensor chip includes one or more resonators, wherein the one or more resonators is substantially in contact with at least a fluid, wherein the at least a fluid includes one or more analytes and the reader device communicatively connected to the photonic sensor chip, wherein the reader device includes at least a light source and the reader device is configured to provide an input optical signal using the at least a light source, receive the one or more sensor signals from the photonic sensor chip and determine one or more characteristics of the one or more analytes of the at least a fluid as a function of the one or more sensor signals and a connecting system, wherein the connecting system is configured to connect the photonic sensor chip and the reader device.

The present disclosure may also discuss a photonic biosensor that could provide an inexpensive, re-usable, and scalable diagnostic solution for sensing of an array of biological analytes with enhanced specificity and sensitivity of detection. Exemplary embodiments illustrating aspects of the present disclosure are described below in the context of several specific examples.

Figure 1:
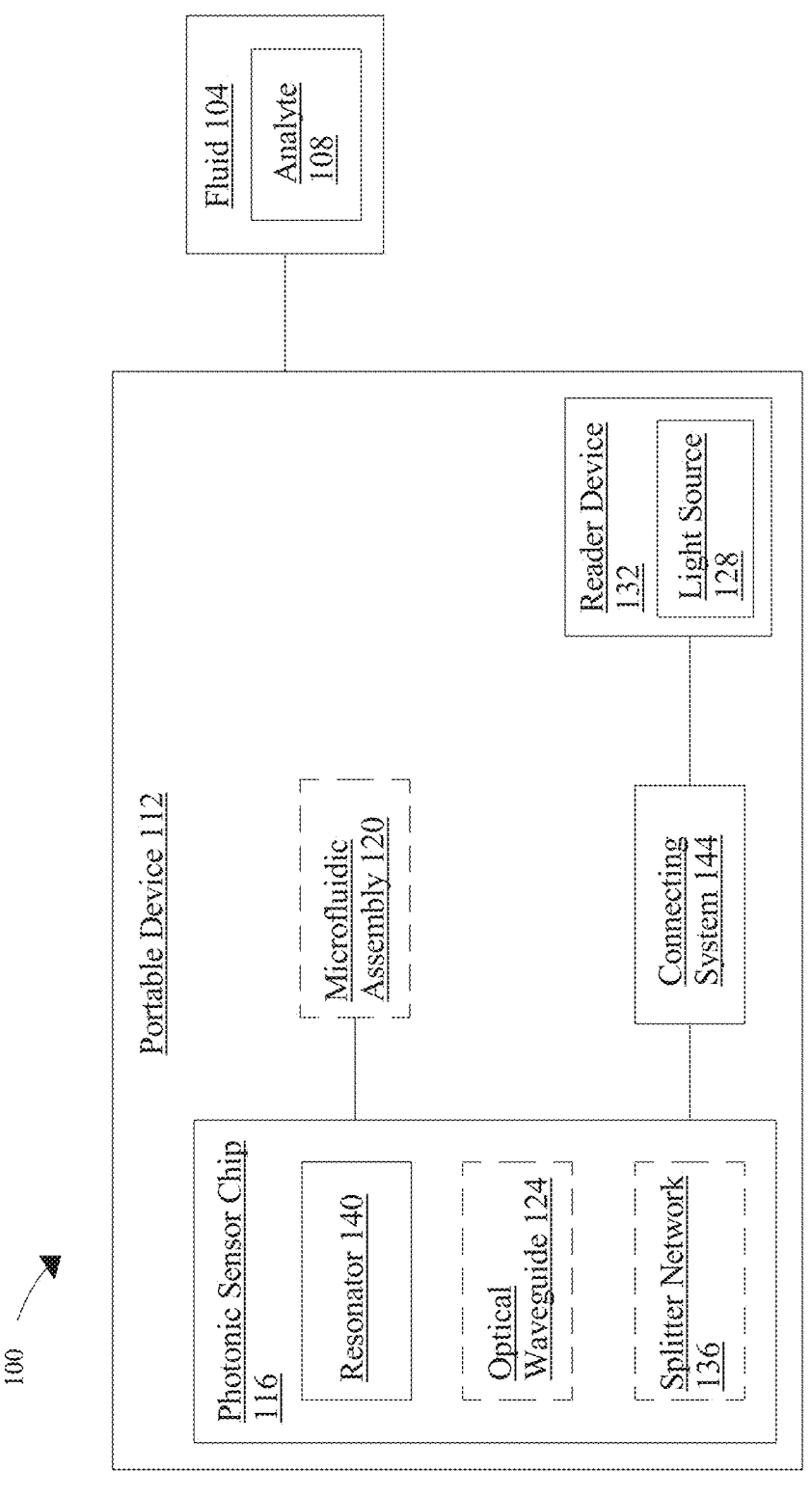
FIG. 1 is a block diagram of an exemplary apparatus for photonic biosensors for multiplexed diagnostics.

Referring now to FIG. 1, a block diagram of an exemplary embodiment of an apparatus 100 for a multiplexed and point-of-care diagnostic of analytes is illustrated. In some embodiments, the apparatus 100 may be reusable. For the purposes of this disclosure, "point-of-care diagnostic" is a technique of diagnosis that allows detection and diagnosis of diseases at or near the patient site. For the purposes of this disclosure, a "patient site" is a patient's physical location at the time of receipt of a sample from the patient's body. For the purposes of this disclosure, a "patient" is any human or animal. For the purposes of this disclosure, "multiplexed diagnostic" is a technique of diagnosis that can detect multiple analytes in a single sample. For the purposes of this disclosure, a "sample" is some quantity of tissue, fluid, or the like extracted from a subject organism, such as without limitation, a human being, and/or a substance derived therefrom. As a non-limiting example, the sample may include serum samples, virology swab samples, biopsy and necropsy tissue, cerebrospinal fluid, whole blood, urine samples, and the like. In some embodiments, the sample may include at least a fluid 104. In some embodiments, at least a fluid 104 includes one or more analytes 108. For the purposes of this disclosure, "fluid" is any sample that has no fixed shape and yields easily to external pressure. Persons skilled in the art, upon reviewing the entirety of this disclosure, may appreciate various samples that may be used for an apparatus 100.

With continued reference to FIG. 1, for the purposes of this disclosure, an "analyte" is a substance that is of interest in an analytical procedure. As a non-limiting example, one or more analytes 108 may include glucose, proteins, hormones, antibodies, and the like. As another non-limiting example, the one or more analytes 108 may include Albumin, C-reactive protein, SARS-COV-2 protein, Thyroxine-binding globulin, Thyroxine-binding prealbumin (transthyretin,) Ceruloplasmin, Haptoglobin, Apolipoprotein A-I (protein of HDL,) Apolipoprotein A-II (another protein of HDL,) Apolipoprotein B-100 (protein of LDL,) Transferrin, Serum free light chains (info from LabCorp,) Antithrombin III, Fibrinogen, Lysozyme, Plasminogen, C3 complement, C4 complement, D-dimer, a1-Fetoprotein (AFP,) a2-Macroglobulin (AMG,) Retinol binding protein, Alpha1-Antitrypsin (A1AT or AAT,) a1-Acid Glycoprotein (or orosomucoid,) cxl-antichymotrypsin (Serpin family A member 3) ghrelin, Hemopexin, Complement factor H, Vitronectin, C4b binding protein (Complement component 4 binding protein beta,) Cysteine rich secretory glycoprotein LCCL domain containing 2 (Crispld2,) Complement C5, Alpha 1-B glycoprotein, Apolipoprotein H, Apolipoprotein A4, Plasminogen, GC vitamin D binding protein (DBP,) Histidine rich glycoprotein, Coagulation factor II, thrombin, Glycosylphosphatidylinositol specific phospholipase Dl, Complement Cls, Fetuin B, Kininogen 1, Complement C9, Gelsolin, Apolipoprotein C3, Serpin family A member 6, Apolipoprotein C1, Paraoxonase 1, Serum amyloid 4, Alpha-2 glycoprotein 1, zinc-binding, Afamin, Apolipoprotein C2, Clusterin, Apolipoprotein E, Serpin family A member 7, Complement component 4 binding protein alpha, Kallikrein B1, Amyloid P component, Renalase, FAD dependent amine oxidase, Thrombospondin 1, Leucine rich alpha-2 glycoprotein 1, Lipopolysaccharide binding protein, Protein S, Retinal binding protein 4, Apolipoprotein F, Ficolin 3, Phospholipase transfer protein, Serpin family F member 1, Adiponectin, ClQ and collagen domain, Insulin such as growth factor binding acid labile subunit, Ficolin 2, Hyaluronan binding protein 2, Mannan binding lectin serine peptidase 1, C-type lectin domain family 3 member B, Coagulation factor V, Complement Clr subcomponent, Lecithin-cholesterol acyltransferase, CDS molecule, Serpin family A member 10, Apolipoprotein L1, Insulin like growth factor binding protein 3, Cholesterol ester transfer protein, CD14, Glutathione peroxidase 3, CD163, Paraoxanase 3, Protein Z, Ficolin 1, Transferrin receptor, ADAM metallopeptidase with thrombospondin type 1 motif 13, Complement factor D, Cystatin C, Apolipoprotein C4, Myeloperoxidase, Mannose binding lectin 2, Complement factor B, C-C motif chemokine ligand 28, Tenascin C, Vascular cell adhesion molecule 1 (VCAMl,) Cathelicidin antimicrobial peptide, Insulin like growth factor binding protein 2, Complement factor H related 3, Insulin like growth factor 2, Complement Clq C chain, Mannan binding lectin serine peptidase 2, Lipase G, C1q and TNF related 9, Fibrinogen alpha chain, Clq and TNF related 6, Von Willebrand factor, Gremlin 1, C1q and TNF related 5, C1q and TNF related 1, Serum amyloid Al, Angiogenin, C1q and TNF related 7, Orosomucoid 2, Angiopoietin like 3, F c receptor like BMP4, Chromogranin A, and the like. Persons skilled in the art, upon reviewing the entirety of this disclosure, may appreciate various analytes 108 that may be used for an apparatus 100. Additional disclosures related to the at least an analyte 108 may be found in International Patent Application No PCT/US2022/037767, filed on Jul. 20, 2022, entitled as "WEARABLE BIOSENSORS FOR SEMI-INVASIVE, REAL-TIME MONITORING OF ANALYTES, AND RELATED METHODS AND APPARATUS," the entirety of which is incorporated herein by reference.

With continued reference to FIG. 1, apparatus 100 includes a portable device 112 configured for point-of-care diagnostics. For the purposes of this disclosure, a "portable device" is device that is a device that is designed to be transported from place to place. In some embodiments, portable device 112 may include a housing. As used in this disclosure, a "housing" refers to an outer structure configured to contain a plurality of components, such as, without limitation, components of apparatus 100 as described in this disclosure. In a non-limiting example, portable device 112 may include an outer casing of apparatus 100. In some cases, the housing may include a durable, lightweight material such as without limitation, plastic, metal, and/or the like. In some embodiments, the housing may be designed and configured to protect sensitive components of apparatus 100 from damage or contamination. In a non-limiting example, the portable device 112 may include one or more flat facets located on the housing configured to constraint at least a photonic sensor chip 116 as described below in this disclosure, wherein the "flat facet" refers to a surface or object that is smooth and even, without any significant curvature or bumps. In another non-limiting example, portable device 112 may include one or more physical notches and/or grooves that allow for precise placement of devices and/or components. In yet another non-limiting example, the portable device 112 may include one or more optical markers or alignment indicators that are visible (through human eye, microscope, any other imaging system, and/or the like) and allow for accurate positioning of devices and/or components. In further non-limiting examples, portable device 112 may include one or more tapered or angled surfaces (of the housing.) The one or more tapered or angled surfaces may be configured to guide a microfluidic assembly 120, as described below in this disclosure, through the portable device 112. In other non-limiting examples, the housing may include one or more surface coatings and/or modifications that reduce the likelihood of unwanted adhesion or interference with external components and/or substances. Additionally, or alternatively, the portable device 112 may further include features such as latches, clips, or other fasteners that help to secure apparatus 100 in place during use.

With continued reference to FIG. 1, a portable device 112 of an apparatus 100 includes a photonic sensor chip 116. For the purposes of this disclosure, "photonic sensor chip" a chip that includes electronic components that form a functional circuit that detects, generates, transports, and processes light. Additionally and without limitation, the photonic sensor chip 116 disclosed herein may be consistent with a photonic integrated circuit (PIC) found in International Patent Application No PCT/US2022/037767 and a sensor device found in U.S. patent application Ser. No. 18/121,712, filed on Mar. 15, 2023, entitled as "APPARATUS AND METHODS FOR PERFORMING MICROFLUIDIC-BASED BIOCHEMICAL ASSAYS,", the entirety of which are incorporated herein by references.

With continued reference to FIG. 1, in some embodiments, a photonic sensor chip 116 may include an optical waveguide 124. For the purposes of this disclosure, an "optical waveguide" is a structure that is designed to confine and guide electromagnetic waves along a path from one point to another. As a non-limiting example, electromagnetic waves may include ultraviolet, x-rays, gamma rays, infrared, microwave, radio waves, visible light, and the like. In some embodiments, the photonic sensor chip 116 may include a plurality of optical waveguide 124. In some embodiments, the optical waveguide 124 may include dielectric materials, silicon, glass, polymer, semiconductor, and the like. In some embodiments, the optical waveguide 124 may include various geometry of the waveguide. As a non-limiting example, the optical waveguide 124 may include a straight waveguide, tapered waveguide, grating waveguide, and the like. In some embodiments, the optical waveguide 124 may include various shapes, including but not limited to rectangular, circular, elliptical cross-sections, and the like. In some embodiments, the optical waveguide 124 may include optical fiber waveguides, transparent dielectric waveguides, liquid light guides, liquid waveguides, light pipe, laser-inscribed waveguide, and the like. In some embodiments, the optical waveguide 124 may include planar, strip, rib, fiber waveguides, and the like. In some embodiments, the optical waveguide 124 may include single-mode, multi-mode, and the like. In some embodiments, the optical waveguide 124 may include various refractive index distributions such as but not limited to step index distribution, gradient index distribution, and the like. For the purposes of this disclosure, "refractive index" of a material is a measure of how much the material can bend, or refract, light as it passes through it.

With continued reference to FIG. 1, in some embodiments, an optical waveguide 124 may include a first edge of the optical waveguide 124. For the purposes of this disclosure, an "first edge of an optical waveguide" is an edge of an optical waveguide 124 that receives light wave from a source. As a non-limiting example, the first edge of an optical waveguide 124 may receive the light wave (also called as an "optical signal," "input optical signal," "light signal" or "light") directly from at least a light source 128 of a reader device 132. As another non-limiting example, the first edge of an optical waveguide 124 may receive the optical signal from a splitter network as described below. As another non-limiting example, the first edge of optical waveguide 124 may receive the optical signal from a fiber-optic cable as described below. In some embodiments, a design and optimization of the first edge of an optical waveguides 124 may depend on the mode profile, polarization state, refractive index of materials used, wavelength of the optical signal of an input source.

With continued reference to FIG. 1, in some embodiments, an optical waveguide 124 may include a second edge of the optical waveguide 124. For the purposes of this disclosure, an "second edge of an optical waveguide" is an edge of an optical waveguide 124 that guides an optical output out. For the purposes of this disclosure, an "optical output" is an optical signal that is output from the second edge of an optical waveguide 124. As a non-limiting example, the second edge of an optical waveguide 124 may output the optical output to at least a photodetector. As another non-limiting example, the second edge of an optical waveguide 124 may output the optical output to the fiber-optic cable. In some embodiments, a design and optimization of the second edge of an optical waveguide 124s may depend on the wavelength of the optical signal, polarization state, refractive index of materials used and/or mode profile of an output source.

With continued reference to FIG. 1, in some embodiments, a photonic sensor chip 116 may include a splitter network 136. For the purposes of this disclosure, a "splitter network" is a device or a network that divides an input optical signal into two or more output optical signals. For the purposes of this disclosure, an "output optical signal" is an optical signal that is output from a splitter network. In an embodiment, each of the two or more output optical signals may include the same power as input power of the input optical signal. In another embodiment, each of two or more output optical signals may include a fraction of the input power of the input optical signal. In some embodiments, the two or more output optical signals may include a fixed power ratio determined by the design of the splitter network 136. For the purposes of this disclosure, "input power" of the input optical signal is amount of electromagnetic energy that is carried by an optical signal. The input power may be measured in units of watts. In some embodiments, a splitting ratio, the wavelength range, the insertion loss, and the polarization dependence may vary for the splitter network 136 (also called as "splitter," or "optical splitter.")

With continued reference to FIG. 1, in some embodiments, a splitter network 136 may include various types of splitter networks 136 such as but not limited to Y-splitter, 1×N splitter, optical power splitter, fiber optic coupler, and the like. For the purposes of this disclosure, a "1×N splitter" is an optical splitter with one input port and multiple output ports. The 1×N splitter may be used to divide an input optical signal into multiple equal parts of two or more output optical signals. For example and without limitation, a 1×2 optical splitter may split the input optical signal into two output optical signals, with each output optical signal having half the power of the input optical signal. For another example and without limitation, a 1×4 optical splitter may split the input optical signal into four output optical signals, with each output optical signal having a quarter of the power of the input optical signal. In some embodiments, the splitter network 136 may be used in reverse as a combiner network. As a non-limiting example, the splitter network 136 may combine multiple input optical signals into a single output optical signal.

With continued reference to FIG. 1, in an embodiment, a splitter network 136 may include a passive optical splitter. For the purposes of this disclosure, a "passive optical splitter" is a type of optical splitter that does not require any external power or active electronic components to split an incoming optical signal. As a non-limiting example, the passive optical splitter may include Fused Biconical Taper (FBT) splitter, Planar Lightwave Circuit (PLC) splitter, Micro-Opto-Electro-Mechanical systems (MOEMS) splitter, Tapered Waveguide splitter, Fused Tapered couplers, Multimode Interference (MMI) splitter, and the like. In an embodiment, the passive optical splitter may be made by fusing and tapering two or more fibers together. In another embodiment, the passive optical splitter may be made by lithographically patterning a waveguide structure on a flat substrate such as but not limited to SOI substrate as described below. In some embodiments, the fibers or waveguides may be designed to split an input optical signal into two or more output optical signals with a predefined splitting ratio.

With continued reference to FIG. 1, in another embodiment, a splitter network 136 may include an active optical splitter. For the purposes of this disclosure, an "active optical splitter" is a type of optical splitter that requires external power and active electronic components to split an incoming optical signal. As a non-limiting example, the active optical splitter may include semiconductor optical amplifiers (SOAs), electro-absorption modulators (EAMs), thermo-optic (TO) devices, and the like. In some embodiments, the active optical splitter may be integrated with a reader device 132.

With continued reference to FIG. 1, a photonic sensor chip 116 includes one or more resonators 140. For the purposes of this disclosure, a "resonator" is a structure made of waveguide that can trap, store, transmit, process electromagnetic waves. In an embodiment, the one or more resonators 140 may include photonic crystal cavities, grating structures, or interferometric structures such as Mach-Zehnder or Michelson interferometers, and the like. For the purposes of this disclosure, a "grating structure" is a structure of any regularly spaced collection of essentially identical, parallel, elongated elements, such as but not limited to optical waveguides. A "period A" of the grating determines the diffraction. As a non-limiting example, the grating structures may include a silicon sub-wavelength grating (SWG). For the purposes of this disclosure, a "sub-wavelength grating" is grating structures with a period A that is sufficiently small compared to the wavelength of light.

Figure 4:
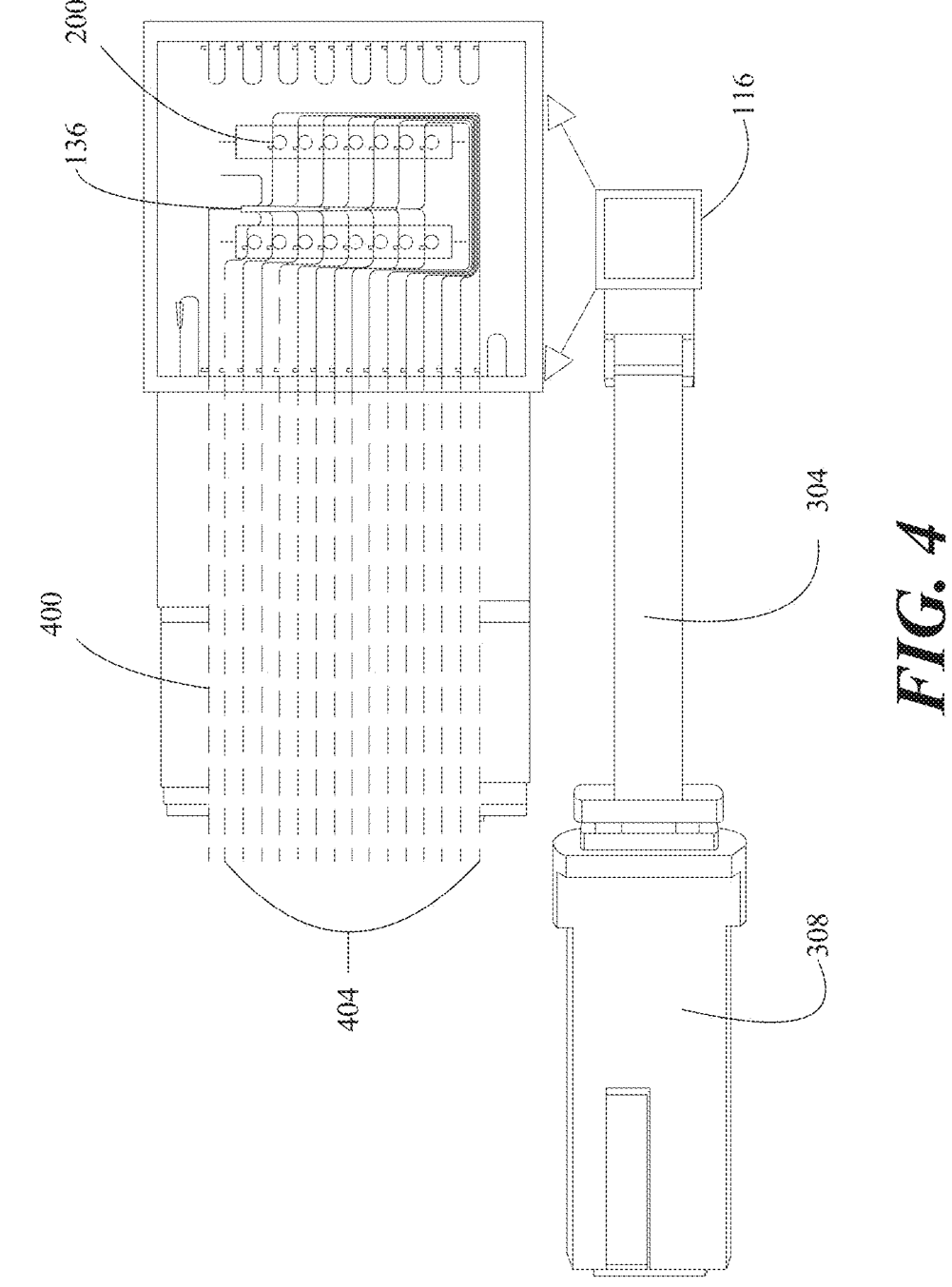
FIG. 4 is an exemplary embodiment of a portion of an apparatus with a photonic sensor chip.

With continued reference to FIG. 1, in some embodiments, one or more resonators 140 may include one or more ring resonators. For the purposes of this disclosure, a "ring resonator" is a waveguide that is a closed loop. In some embodiments, the one or more resonators 140 may include various sizes and shapes of the loop (or a ring) and refractive index. In some embodiments, one or more ring resonators may be coupled with an optical waveguide 124. As a non-limiting example, one or more ring resonators may be in contact with the optical waveguide 124. As another non-limiting example, the one or more ring resonators may include a gap between the one or more ring resonators and the optical waveguide 124. In some embodiments, one or more ring resonators may use the principle of resonant wave coupling to filter or select certain wavelengths of light. In some embodiments, the photonic sensor chip 116 may include one or more arrays of one or more ring resonators. An example configuration of the one or more arrays of the one or more ring resonators is shown in FIG. 4. In an embodiment, each of the one or more ring resonators may detect the same one or more analytes 108 of at least a fluid 104. In another embodiment, each of the one or more ring resonators may detect different one or more analytes 108 of the at least a fluid 104. As a non-limiting example, one ring resonator of the one or more ring resonators may detect SARS-COV-protein while another ring resonator of the one or more ring resonators detects glucose. When light is input into the loop (or the ring) of one or more ring resonators, the light may circulate around the loop multiple times due to total internal reflection, creating a standing wave pattern with constructive and/or destructive interference. Then, the one or more resonators 140 may output an optical output. Because only a select few wavelengths are at resonance within the loop of the one or more ring resonators, the one or more ring resonators may function as a filter. In an embodiment, the light (or an input optical signal) may be input to a first edge of an optical waveguide 124 of an optical waveguide 124, where the light may be from a fiber-optic cable with a PM fiber delivering the light from at least a light source 128. In another embodiment, two or more output optical signals (the light) from a splitter network 136 that divided the input optical signal from the at least a light source 128 may be input to the first edge of an optical waveguide 124 of the optical waveguide 124. In another embodiment, an optical output may be output from a second edge of an optical waveguide 124 of the optical waveguide 124 to at least a photodetector. As a non-limiting example, the optical output may be output from the second edge of an optical waveguide 124 of the optical waveguide 124 to the at least a photodetector, then, to a reader device.

With continued reference to FIG. 1, in some embodiments, one or more ring resonators may include a single-ring resonator, double-ring resonator, add-drop filter, Vernier ring resonator, Bragg grating ring resonator, and the like. In some embodiments, one or more ring resonators may include a micro-ring resonator. For the purposes of this disclosure, a "micro-ring resonator" is a miniaturized version of the ring resonator. In some embodiments, the micro-ring resonator may be fabricated with a silicon or silicon-on-insulator (SOI) substrate using photolithography, etching, deposition, and/or other microfabrication techniques. For the purposes of this disclosure, "silicon-on-insulator substrate" is a type of semiconductor substrate. As a non-limiting example, the SOI substrate may include a thin layer of silicon, such as but not limited to silicon dioxide, on top of a layer of insulating material which is itself on top of a bulk silicon substrate. In some embodiments, the SOI substrate may reduce capacitance and parasitic effects, provide better isolation between devices, improve radiation hardness, and the like. In some embodiments, the SOI substrate may be fabricated for optical waveguides 124, ring resonators, splitter networks 136, and other photonic structures.

With continued reference to FIG. 1, in some embodiments, one or more resonators 140 may include a respective layer of binding ligands. For the purposes of this disclosure, a "binding ligand" is a ligand that is capable of binding an analyte. Additional disclosure related to the binding ligand disclosed herein may be found in International Patent Application No PCT/US2022/037767.

With continued reference to FIG. 1, in some embodiments, a photonic sensor chip 116 may utilize evanescent field of an optical waveguide 124 and one or more resonators 140 to probe properties and/or characteristics of the surrounding medium such as but not limited to one or more analytes 108 of at least a fluid 104. For the purposes of this disclosure, "evanescent field" is a type of electromagnetic field that exists outside the core of an optical waveguide. The evanescent field may decay exponentially with distance from the core and may carry less energy than the propagating mode inside the waveguide. When the waveguide 124 and/or the one or more resonators 140 is brought close to the one or more analytes 108 of the at least a fluid 104, where the one or more analytes 108 are immobilized on the surface of the waveguide 124 and/or the one or more resonators 140 such as but not limited to with binding ligands, one or more characteristics of the one or more analytes 108 such as but not limited to their concentration, binding kinetics, conformational changes, or the like, may be probed using the evanescent field. Additional disclosure related to various methods to sense the one or more analytes may be found in International Patent Application No PCT/US2022/037767.

With continued reference to FIG. 1, in some embodiments, a photonic sensor chip 116 may include at least a photodetector. In some cases, the photonic sensor chip 116 may include a plurality of photodetectors, for instance a first photodetector and a second photodetector. In some cases, the first photodetector and/or the second photodetector may be configured to measure one or more of first optical output and second optical output, from a first waveguide 124 and a second waveguide 124, respectively, such as but not limited to an second edge of an optical waveguide 124. The at least a first photodetector may be configured to convert the first optical output into a first sensor signal as a function of variance of an optical property of the first waveguide 124, where the first sensor signal may include without limitation any voltage and/or current waveform. Additionally, or alternatively, the photonic sensor chip 116 may include a second photodetector located down beam from the second waveguide 124. In some embodiments, the second photodetector may be configured to measure a variance of an optical property of second waveguide 124 and convert the second optical output into a second sensor signal as a function of the variance of the optical property of the second waveguide 124.

With continued reference to FIG. 1, as used in this disclosure, a "photodetector" is any device that is sensitive to light and thereby able to detect light. In some cases, the at least a photodetector may include a photodiode, a photoresistor, a photosensor, a photovoltaic chip, and the like. In some cases, the at least a photodetector may include a Germanium-based photodiode. The at least a photodetector may include, without limitation, Avalanche Photodiodes (APDs), Single Photon Avalanche Diodes (SPADs), Silicon Photomultipliers (SiPMs), Photo-Multiplier Tubes (PMTs), Micro-Channel Plates (MCPs), Micro-Channel Plate Photo-multiplier Tubes (MCP-PMTs), Indium gallium arsenide semiconductors (InGaAs), photodiodes, and/or photosensitive or photon-detecting circuit elements, semiconductors and/or transducers. "Avalanche Photo Diodes (APDs)," as used herein, are diodes (e.g., without limitation p-n, p-i-n, and others) reverse biased such that a single photon generated carrier can trigger a short, temporary "avalanche" of photocurrent on the order of milliamps or more caused by electrons being accelerated through a high field region of the diode and impact ionizing covalent bonds in the bulk material, these in turn triggering greater impact ionization of electron-hole pairs. APDs may provide a built-in stage of gain through avalanche multiplication. When the reverse bias is less than the breakdown voltage, the gain of the APD may be approximately linear. For silicon APDs, this gain may be on the order of 10-100. Material of APD may contribute to gains. Germanium APDs may detect infrared out to a wavelength of 1.7 micrometers. InGaAs may detect infrared out to a wavelength of 1.6 micrometers. Mercury Cadmium Telluride (HgCdTe) may detect infrared out to a wavelength of 14 micrometers. An APD reverse biased significantly above the breakdown voltage may be referred to as a Single Photon Avalanche Diode, or SPAD. In this case, the n-p electric field may be sufficiently high to sustain an avalanche of current with a single photon, hence referred to as "Geiger mode." This avalanche current rises rapidly (sub-nanosecond), such that detection of the avalanche current can be used to approximate the arrival time of the incident photon. The SPAD may be pulled below breakdown voltage once triggered in order to reset or quench the avalanche current before another photon may be detected, as while the avalanche current is active carriers from additional photons may have a negligible effect on the current in the diode.

With continued reference to FIG. 1, in some cases, at least a photodetector may include a photosensor array, for example without limitation a one-dimensional array. The photosensor array may be configured to detect a variance in an optical property of waveguide. In some cases, first photodetector and/or second photodetector may be wavelength dependent. For instance, and without limitation, first photodetector and/or second photodetector may have a narrow range of wavelengths to which each of first photodetector and second photodetector are sensitive. As a further non-limiting example, each of first photodetector and second photodetector may be preceded by wavelength-specific optical filters such as bandpass filters and/or filter sets, or the like; in any case, a splitter may divide output from optical matrix multiplier as described below and provide it to each of first photodetector and second photodetector. Alternatively, or additionally, one or more optical elements may divide output from waveguide prior to provision to each of first photodetector and second photodetector, such that each of first photodetector and second photodetector receives a distinct wavelength and/or set of wavelengths. For example, and without limitation, in some cases a wavelength demultiplexer may be disposed between waveguides and first photodetector and/or second photodetector; and the wavelength demultiplexer may be configured to separate one or more lights or light arrays dependent upon wavelength. As used in this disclosure, a "wavelength demultiplexer" is a device that is configured to separate two or more wavelengths of light from a shared optical path. In some cases, a wavelength demultiplexer may include at least a dichroic beam splitter. In some cases, a wavelength demultiplexer may include any hot mirror, a cold mirror, a short-pass filter, a long pass filter, a notch filter, and the like. An exemplary wavelength demultiplexer may include part No. WDM-11P from OZ Optics of Ottawa, Ontario, Canada. Further examples of demultiplexers may include, without limitation, gratings, prisms, and/or any other devices and/or components for separating light by wavelengths that may occur to persons skilled in the art upon reviewing the entirety of this disclosure. In some cases, at least a photodetector may be communicative with computing device, such that a sensed signal such as but not limited to one or more sensor signals may be communicated with computing device of a reader device 132.

With continued reference to FIG. 1, in some embodiments, a photonic sensor chip 116 may further include a microfluidic assembly 120. For the purposes of this disclosure, a "microfluidic assembly" is an assembly that is configured to act upon fluids at a small scale, such as without limitation a sub-millimeter scale. At small scales, surface forces may dominate volumetric forces. In some embodiments, the microfluidic assembly 120 may be on atop of one or more resonators 140 of a photonic sensor chip 116. Additional disclosure related to the microfluidic subassembly may be found in U.S. patent application Ser. No. 18/121,712 and in U.S. patent application Ser. No. 17/859,932, filed on Jul. 7, 2022, entitled "SYSTEM AND METHODS FOR FLUID SENSING USING PASSIVE FLOW," the entirety of which is incorporated herein by references.

With continued reference to FIG. 1, in some embodiments, a microfluidic assembly 120 may include at least a microfluidic feature. As used in this disclosure, a "microfluidic feature" is a structure within microfluidic assembly 120 that is designed and/or configured to manipulate one or more fluids at micro scale. In a non-limiting example, microfluidic feature may include, without limitation, reservoir, microfluidic channel, conjugate pad, and the like. In some cases, microfluidic feature may enable a precise manipulation of fluids and samples in a controlled and/or reproducible manner within microfluidic assembly 120. In some embodiments, microfluidic feature of microfluidic assembly 120 may be designed and arranged based on particular needs. In other embodiments, microfluidic feature of microfluidic assembly 120 may be varied depending on the type of at least a fluid 104 being used, that is directly contact with microfluidic feature. In a non-limiting example, attributes of microfluidic feature such as, without the size and/or shape of the substrate may be determined as a function of specific assay protocols.

With continued reference to FIG. 1, microfluidic feature includes at least a reservoir. The at least a reservoir may be configured to contain at least a fluid 104. In a non-limiting example, at least a fluid 104 may include a sample fluid to be analyzed from a subject; for instance, and without limitation, the at least a reservoir of the microfluidic assembly 120 may contain a blood sample taken from a patient.

Alternatively, or additionally, the at least a fluid 104 may include one or more suspensions and/or solutions of reagents, molecules, or other items to be analyzed and/or utilized, including without limitation monomers such as individual nucleotides, amino acids, or the like, one or more buffer solutions and/or saline solutions for rinsing steps, and/or one or more analytes to be detected and/or analyzed. The at least a fluid 104 and/or microfluidic assembly 120 may be used, without limitation, in processes as disclosed in U.S. Nonprovisional application Ser. No. 17/337,931, filed on Jun. 3, 2021 and entitled "METHODS AND SYSTEMS FOR MONOMER CHAIN FORMATION," and/or as disclosed in U.S. Nonprovisional application Ser. No. 17/403, 480, filed on Aug. 16, 2021 and entitled "TAGGED-BASE DNA SEQUENCING READOUT ON WAVEGUIDE SURFACES," the entirety of each of which is incorporated herein by reference. The at least a reservoir may have at least an inlet, at least an outlet, or both. The at least a reservoir may further include, without limitation, a well, a channel, a flow path, a flow cell, a pump, and the like. In a non-limiting example, the at least a fluid 104 may be input through the at least an inlet into the at least a reservoir and/or output through the at least an outlet. At least an outlet may be connected to other components and/or devices within the microfluidic assembly 120; for instance, and without limitation, at least an outlet may be connected to other microfluidic feature such as microfluidic channel.

With continued reference to FIG. 1, in some embodiments, a microfluidic assembly 120 may further include at least a flow component connected with at least a microfluidic feature configured to flow at least a fluid through a photonic sensor chip 116. In some embodiments, at least a flow component may include a passive flow component configured to initiate a passive flow process. As used in this disclosure, a "passive flow component" is a component, typically of a microfluidic assembly, that imparts a passive flow on at least a fluid, wherein the "passive flow," for the purpose of this disclosure, is flow of the at least a fluid, which is induced absent any external actuators, fields, or power sources. As used in this disclosure, a "passive flow process" is a plurality of actions or steps taken on passive flow component in order to impart a passive flow on at least a fluid. The passive flow component may employ one or more passive flow techniques in order to initiate passive flow process; for instance, and without limitation, passive flow techniques may include osmosis, capillary action, surface tension, pressure, gravity-driven flow, hydrostatic flow, vacuums, and the like. The passive flow component may be in fluidic communication with at least a reservoir. The passive flow component may be configured to flow the at least a fluid stored in the at least a reservoir with predetermined flow properties. In a non-limiting example, the passive flow component may be consistent with any passive flow component described in U.S. patent application Ser. No. 17/859,932, filed on Jul. 7, 2022, entitled "SYSTEM AND METHODS FOR FLUID SENSING USING PASSIVE FLOW," the entirety of which is incorporated herein by reference.

With continued reference to FIG. 1, in other embodiments, at least a flow component may include an active flow component configured to initiate an active flow process. As used in this disclosure, an "active flow component" is a component that imparts an active flow on at least a fluid, wherein the "active flow," for the purpose of this disclosure, is flow of the at least a fluid which is induced by external actuators, fields, or power sources. As used in this disclosure, an "active flow process" is a plurality of actions or steps taken on active flow component in order to impart active flow on at least a fluid. In some embodiments, the active flow component is in fluidic communication with at least a reservoir. In a non-limiting example, the active flow component may include one or more pumps. The one or more pumps may include a substantially constant pressure pump (e.g., centrifugal pump) or a substantially constant flow pump (e.g., positive displacement pump, gear pump, and the like). The one or more pumps can be hydrostatic or hydrodynamic. As used in this disclosure, a "pump" is a mechanical source of power that converts mechanical power into fluidic energy. The one or more pumps may generate flow with enough power to overcome pressure induced by a load at a pump outlet. The one or more pumps may generate a vacuum at a pump inlet, thereby forcing fluid from at least a reservoir into the pump inlet to the one or more pumps pump and by mechanical action delivering the at least a fluid 104 to a pump outlet. The hydrostatic pumps may include positive displacement pumps. The hydrodynamic pumps can be fixed displacement pumps, in which displacement may not be adjusted, or variable displacement pumps, in which the displacement may be adjusted. Exemplary non-limiting pumps include gear pumps, rotary vane pumps, screw pumps, bent axis pumps, inline axial piston pumps, radial piston pumps, and the like. The one or more pumps may be powered by any rotational mechanical work source, for example without limitation and electric motor or a power take off from an engine. The one or more pumps may be in fluidic communication with at least a reservoir. In some cases, at least a reservoir may be unpressurized and/or vented. Alternatively, at least a reservoir may be pressurized and/or sealed; for instance, by alignment component such as, without limitation, a sealer.

With continued reference to FIG. 1, a portable device 112 includes a reader device 132. For the purposes of this disclosure, a "reader device" is a device that processes signals for, generated by, and/or received by a photonic sensor chip. In some embodiments, the reader device 132 may include a housing as described above. The reader device 132 is communicatively connected to the photonic sensor chip 116. In some embodiments, the reader device 132 may be connected with the photonic sensor chip 116 using a connecting system as described below. For the purposes of this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, a reader device 132 may include a computing device. In some embodiments, a processor and a memory communicatively connected to the processor may be included in the computing device. The computing device may include any computing device as described in this disclosure, including without limitation a microcontroller, microprocessor, digital signal processor (DSP) and/or system on a chip (SoC) as described in this disclosure. The computing device may include, be included in, and/or communicate with a mobile device such as a mobile telephone or smartphone. The computing device may include a single computing device operating independently, or may include two or more computing device operating in concert, in parallel, sequentially or the like; two or more computing devices may be included together in a single computing device or in two or more computing devices. The computing device may interface or communicate with one or more additional devices as described below in further detail via a network interface device. Network interface device may be utilized for connecting the computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a computing device or cluster of computing devices in a first location and a second computing device or cluster of computing devices in a second location. The computing device may include one or more computing devices dedicated to data storage, security, distribution of traffic for load balancing, and the like. the computing device may distribute one or more computing tasks as described below across a plurality of computing devices of computing device, which may operate in parallel, in series, redundantly, or in any other manner used for distribution of tasks or memory between computing devices. the computing device may be implemented, as a non-limiting example, using a "shared nothing" architecture.

With continued reference to FIG. 1, a computing device may be designed and/or configured to perform any method, method step, or sequence of method steps in any embodiment described in this disclosure, in any order and with any degree of repetition. For instance, the computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. The computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, in some embodiments, a reader device 132 may include one or more elements of dedicated signal processing hardware and/or software modules. This may include filters, filter banks including analysis and synthesis banks, fast Fourier Transform (FFT) calculation modules, signal generators, matrix operation calculators, or the like. In some embodiments, the reader device 132 may be configured to perform one or more signal processing steps on a signal, where the signal is any signal disclosed in the entirety of this disclosure. As used in this disclosure, a "signal" is any intelligible representation of data, for example from one device to another. A signal may include an optical signal, a hydraulic signal, a pneumatic signal, a mechanical signal, an electric signal, a digital signal, an analog signal and the like. In some cases, a signal may be used to communicate with a computing device, for example by way of one or more ports. In some cases, a signal may be transmitted and/or received by a computing device, for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

With continued reference to FIG. 1, as a non-limiting example, a reader device 132 may analyze, modify, and/or synthesize a signal representative of characteristic. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which may vary continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. In some embodiments, a filter bank may be used, such as but not limited to analysis banks, synthesis banks, FFT filter banks, and the like. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 1, a reader device 132 includes at least a light source 128. The reader device 132 is configured to provide an input optical signal using at least one light source 128. For the purposes of this disclosure, an "input optical signal" is an optical signal that includes electromagnetic radiation. In some embodiments, the input optical signal may be transmitted over optical fibers. As used in this disclosure, a "light source" is any device configured to emit electromagnetic radiation. As a non-limiting example, electromagnetic radiation may include ultraviolet (UV,) visible light, infrared light, and the like. At least a light source 128 may control propagation, direction, polarization, intensity of light waves. In some embodiments, the photonic sensor chip 116 may include lenses, mirrors, prisms, filters, optical fibers, and the like. In some embodiments, at least a light source 128 may be tuned across the resonances of elements of a photonic sensor chip 116. In some cases, at least a light source 128 may include a coherent light source 128, which is configured to emit coherent light, for example a laser. In some cases, at least a light source 128 may include a non-coherent light source 128 configured to emit non-coherent light, for example a light emitting diode (LED). In some cases, at least a light source 128 may emit a light having substantially one wavelength. In some cases, the at least a light source 128 may emit the light having a wavelength range. The light may have a wavelength in an ultraviolet range, a visible range, a near-infrared range, a mid-infrared range, and/or a far-infrared range. For example, in some cases the light may have a wavelength within a range from about 100 nm to about 20 micrometers. In some cases, the light may have a wavelength within a range of about 400 nm to about 2,500 nm. The at least a light source 128 may include, one or more diode lasers, which may be fabricated, without limitation, as an element of an integrated circuit; diode lasers may include, without limitation, a Fabry Perot cavity laser, which may have multiple modes permitting outputting light of multiple wavelengths, a quantum dot and/or quantum well-based Fabry Perot cavity laser, an external cavity laser, a mode-locked laser such as a gain-absorber system, configured to output light of multiple wavelengths, a distributed feedback (DFB) laser, a distributed Bragg reflector (DBR) laser, an optical frequency comb, and/or a vertical cavity surface emitting laser. At least a light source 128 may additionally or alternatively include a light-emitting diode (LED), an organic LED (OLED) and/or any other light emitter. In some cases, at least a light source 128 may be configured to couple light into a photonic sensor chip 116 for instance into one or more waveguide described above.

With continued reference to FIG. 1, a reader device 132 is configured to receive one or more sensor signals from a photonic sensor chip 116. For the purposes of this disclosure, a "sensor signal" is a signal obtained from a photonic sensor chip that is related to one or more analytes of at least a fluid. As a non-limiting example, the sensor signal may include an optical signal, electronic signal, and the like. For example and without limitation, the optical signal may include an optical output from a second edge of an optical waveguide 124 of an optical waveguide 124. For another example and without limitation, the electronic signal may include a signal from at least a photodetector of the photonic sensor chip 116. As another non-limiting example, one or more sensor signals may include a resonance wavelength shift. For the purposes of this disclosure, a "resonance wavelength shift" is a change in resonant wavelength of a photonic sensor chip, such as but not limited to a ring resonator, due to one or more analytes of at least a fluid. A non-limiting example of the resonance wavelength shift of the micro-ring resonator of the photonic sensor chip 116 is shown in FIG. 2.

With continued reference to FIG. 1, in some embodiments, a reader device 132 may receive one or more sensor signals from a photonic sensor chip 116 as the reader device 132 provides an input optical signal to the photonic sensor chip 116. In an embodiment, the reader device 132 may receive the one or more sensor signals, such as but not limited to an output signal, from an optical waveguide 124, such as but not limited to a second edge of an optical waveguide 124 of the photonic sensor chip 116 using an optical fiber. In another embodiment, the reader device 132 may receive one or more sensor signals from at least a photodetector of the photonic sensor chip 116. As a non-limiting example, the optical fiber and/or the at least a photodetector may receive the output signal using a vertical coupling, edge coupling, a grating coupler, or any couplers thereof. For the purposes of this disclosure, a "vertical coupling" is a process of coupling light from an optical waveguide or resonator to a photodetector or optical fiber located in close proximity and vertically to the waveguide or the resonator. As a non-limiting example, in the vertical coupling, the optical waveguide 124 or one or more resonators 140 and the optical fibers may be positioned perpendicular to each other, and the light propagating through the waveguide may be directed upwards towards the optical fibers or the at least a photodetector. For the purposes of this disclosure, an "edge coupling" is a process of coupling light from an optical waveguide or resonator to a photodetector or optical fiber located in close proximity and on the edge of the waveguide or the resonator. As a non-limiting example, in the edge coupling, the optical waveguide 124 or one or more resonators 140 and the optical fibers may be positioned horizontally to each other, and the light propagating through the waveguide may be directed towards the optical fibers or the at least a photodetector. For the purposes of this disclosure, a "grating coupler" is an optical component that is used to couple light into and out of an optical waveguide. In some embodiments, the vertical coupling, edge coupling, and the grating coupler may be utilized to input an input optical signal into the optical waveguide. Additionally, vertical coupling, edge coupling, the grating coupler may be implemented in any other components of the photonic sensor chip 116 and the reader device 132.

With continued reference to FIG. 1, a reader device 132 is configured to determine one or more characteristics of one or more analytes 108 of at least a fluid 104 as a function of one or more sensor signals. In some embodiments, the reader device 132 may determine one or more characteristics of the one or more analytes 108 of the at least a fluid 104 as the reader device 132 received one or more sensor signals from the photonic sensor chip 116. In some embodiments, the reader device 132 may include at least a photodetector. At least a photodetector of the reader device 132 disclosed herein may be consistent with any photodetectors described in the entirety of this disclosure. As a non-limiting example, when the reader device 132 receives an optical output, the at least a photodetector of the reader device 132 may receive the optical output and convert the optical output to one or more sensor signals to determine the one or more characteristics of the one or more analytes 108 of the at least a fluid 104. As a non-limiting example, the one or more characteristics of the one or more analytes 108 of the at least a fluid 104 may include presences of one or more analytes 108 in the at least a fluid, concentration level of the one or more analytes 108 in the at least a fluid 104, and the like. The one or more characteristics of the one or more analytes 108 may be determined as a function of a change in a resonance wavelength, change in optical wavelength, change of concentration level, and the like. For example and without limitation, a shift in the resonance wavelength of one or more resonators 140 may indicate the presence of the one or more analytes 108 of interest. Additional disclosure related to the one or more characteristics of the one or more analytes 108 and/or the methods to determine the one or more characteristics of the one or more analytes 108 may be found in International Patent Application No PCT/US2022/037767.

With continued reference to FIG. 1, portable device 112 of an apparatus 100 includes a connecting system 144. For the purposes of this disclosure, a "connecting system" is a system that connects a photonic sensor chip to a reader device. In some embodiments, the connecting system 144 may include a wavelength-division multiplexing (WDM) system. For the purposes of this disclosure, a "wavelength-division multiplexing system" is a technology which multiplexes a number of optical signals onto a single optical fiber by using different wavelengths of light. The WDM system may be based on a principle that different wavelengths of light can travel through an optical fiber without interfering with each other, making it possible to transmit multiple signals over a single fiber. In some embodiments, by using different wavelengths to carry different signals, a WDM system may increase the capacity of a single fiber by a factor equal to the number of wavelengths used. In some embodiments, the WDM system may allow bidirectional communications over a single strand of fiber, also called wavelength-division duplexing, as well as multiplication of capacity. In some embodiments, the WDM system may include coarse wavelength-division multiplexing (CWDM) and dense wavelength-division multiplexing (DWDM).

With continued reference to FIG. 1, in some embodiments, a portable device 112 may include a fiber-optic cable (also called as "optical cable," or "optic cable"). For the purposes of this disclosure, a "fiber-optic cable" is a cable that includes one or more optical fibers (also called "optic fiber" or "fiber") that are used to transmit optical signals. In some embodiments, the fiber-optic cable may transmit any signal disclosed in the entirety of this disclosure, such as but not limited to an input optical signal, output optical signal, sensor signal, and the like. In some embodiments, the fiber-optic cable may be implemented with any elements of a photonic sensor chip 116 and/or a reader device 132 disclosed in the entirety of this disclosure such as but not limited to an first edge of an optical waveguide 124, second edge of an optical waveguide 124, photodetector, and the like. In some embodiments, a connecting system may further include a ribbon cable. For the purposes of this disclosure, a "ribbon cable" is a fiber-optic cable with a plurality of optical fibers running parallel to each other on the same flat plane. In some embodiments, the ribbon cable may connect a multi-fiber push on connector (MPO) as described below and the photonic sensor chip 116 to connect the photonic sensor chip 116 and the reader device 132. In some embodiments, the fiber-optic cable may include single-mode fibers (SMF), multimode fibers (MF), and the like. As a non-limiting example, the connecting system 144 may include the single-mode fiber to input an input optical signal into the photonic sensor chip 116. As another non-limiting example, the connecting system 144 may include the multimode fibers to carry one or more sensor signals and/or an optical output out from the photonic sensor chip 116 to the reader device 132. In some embodiments, the connecting system 144 may include one single-mode fiber and a plurality of multimode fibers, where a number of the plurality of multimode fibers may be correspond to a number of one or more resonators 140, such as but not limited to one or more micro-ring resonators, used in the photonic sensor chip 116.

With continued reference to FIG. 1, for the purposes of this disclosure, "optical fiber" is a flexible fiber that is used to transmit light signals. In some embodiments, the optical fiber may include glass, plastic, and the like. In some embodiments, the optical fiber may include a core, cladding, and coating (also called as "buffer coating.") For the purposes of this disclosure, a "core" of the optical fiber is a central part of the fiber through which the light travels, while a "cladding" surrounds the core and helps to reflect the light back into the core, keeping it confined within the fiber, which is a layer of material with a lower refractive index than the core. The "coating" of the optical fiber surrounds the cladding and provides mechanical protection and insulation to the fiber. The optical fiber may use the principle of total internal reflection to guide the light through the fiber. When the light enters the core of the fiber at an angle greater than a critical angle, the light may be reflected back into the core and continues to travel along the fiber. For the purposes of this disclosure, a "critical angle" is the minimum angle of incidence at which light is totally reflected back into the same medium, instead of being refracted. In some embodiments, the fiber-optic cable may further include strength member such as but not limited to Kevlar fibers, outer jacket, water-resistant jelly casing, steel wires, copper tubing, and/or the like.

With continued reference to FIG. 1, in some embodiments, a fiber-optic cable may include a polarization-maintaining optical fiber (PM fiber). For the purposes of this disclosure, a "polarization-maintaining optical fiber" is a type of optical fiber that is designed to maintain the polarization state of light propagating through the optical fiber. In some embodiments, the PM fiber may transmit any signal disclosed in the entirety of this disclosure, such as but not limited to an input optical signal, output optical signal, sensor signal, and the like. In some embodiments, the PM fiber may be implemented with any elements of a photonic sensor chip 116 disclosed in the entirety of this disclosure such as but not limited to at least a light source 128, a splitter network 136, an optical waveguide 124, and the like. As a non-limiting example, the PM fiber may receive an input optical signal from at least a light source 128. As another non-limiting example, the PM fiber may transmit the input optical signal to the splitter network 136. As another non-limiting example, the PM fiber may transmit the input optical signal to the waveguide. In the PM fiber, the fiber's core may include elliptical or rectangular in shape, and the core may be surrounded by a cladding that has a higher refractive index than the core. The fiber's asymmetric shape may cause the polarization of the light to be aligned along a specific axis of the fiber, known as a slow axis. The slow axis may be aligned with a mechanical feature of the fiber, such as a stress rod or a side-hole, which may create a birefringent effect in the fiber. The birefringent effect may cause the refractive index of the fiber to be different for the two orthogonal polarizations of the light, which enables the fiber to maintain the polarization state of the light propagating through it.

With continued reference to FIG. 1, a connecting system 144 may include a fiber optic connector. For the purposes of this disclosure, a "fiber optic connector" is a device used to join optical fibers together. As a non-limiting example, the fiber optic connector may include a multi-fiber push on (MPO) connectors, square connector (SC), straight tip (ST) connector, ferrule core (FC) connector, lucent connector (LC), MT-RJ connector, and the like. For the purposes of this disclosure, a "multi-fiber push on connector" is a connector that connects multiple optical fibers together and uses a push-pull latching mechanism. In some embodiments, the connecting system 144 may include a fiber optic adapter. For the purposes of this disclosure, a "fiber optic adapter" is a device to join fiber optic connectors. As a non-limiting example, the fiber optic adapter may include simplex adapter, duplex adapter, quad adapter, hybrid adapter, bare fiber adapter, and the like. As another non-limiting example, the fiber optic adapter may include MPO adapter, SC adapter, ST adapter, FC adapter, LC adapter, and the like.

Figures 2A, 2B, 2C:
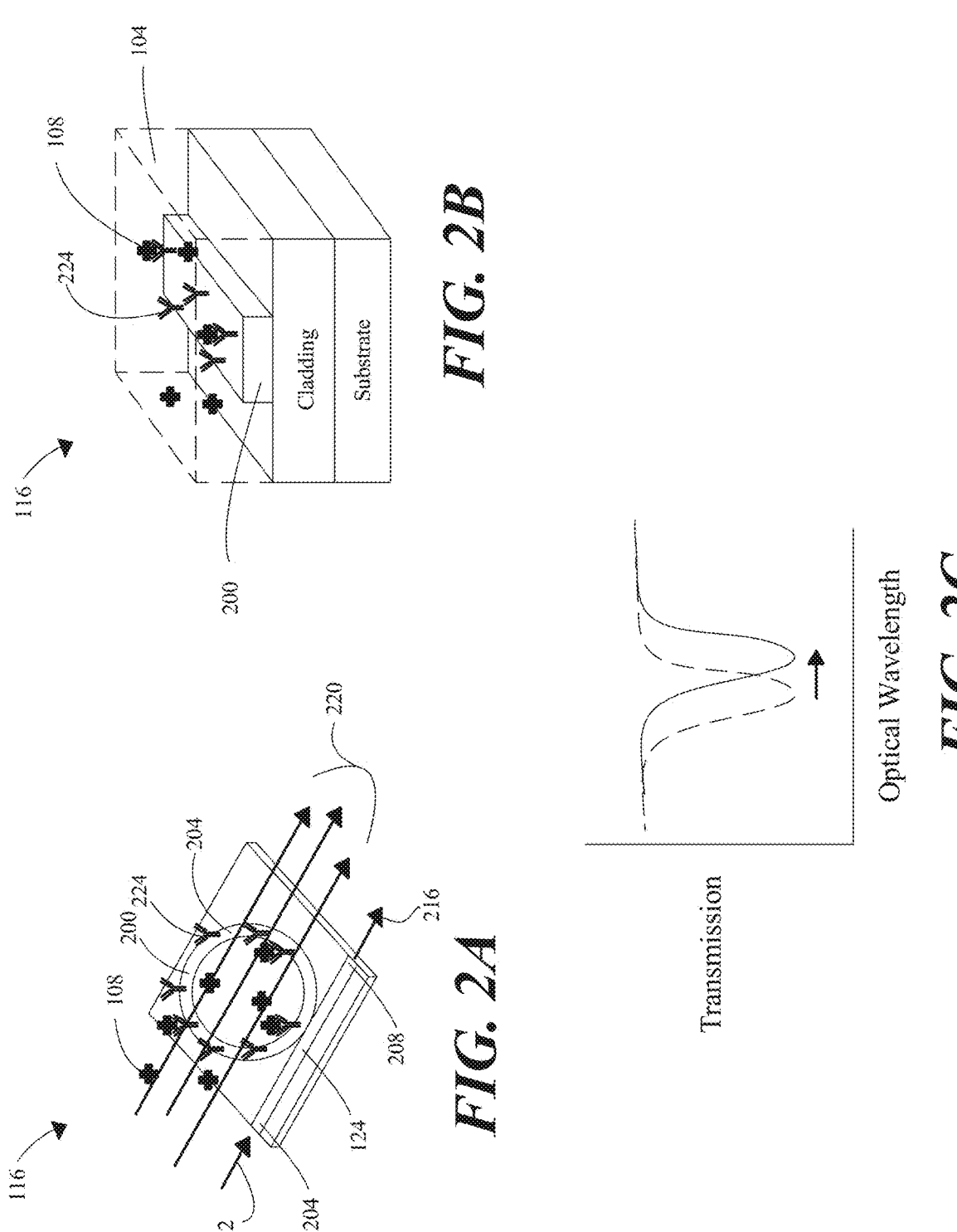
FIG. 2A is an exemplary embodiment of a portion of a photonic sensor chip with a micro-ring resonator and a portion of an optical waveguide.
FIG. 2B is an exemplary embodiment of a portion of a photonic sensor chip with a micro-ring resonator and a portion of an optical waveguide.
FIG. 2C is an exemplary schematic of a shift in resonance wavelength detected by a reader device.

Referring now to FIG. 2A-2C, FIG. 2A illustrates a portion of a photonic sensor chip 116 with a micro-ring resonator 200 and a portion of an optical waveguide 124. FIG. 2B illustrates a cross section of the portion of the photonic sensor chip 116. In some embodiments, the photonic sensor chip 116 may include an optical waveguide 124 with a first edge 204 of the optical waveguide 124 and a second edge 208 of the optical waveguide 124. In an embodiment, an input optical signal 212 may be input to the first edge 204 of the optical waveguide 124. In another embodiment, an optical output 216 may be carried out from the second edge 208 of the optical waveguide 124. In some embodiments, the photonic sensor chip 116 may include an array of ring resonators such as but not limited to micro-ring resonators 200, splitter network 136, and optical read-out using an edge or vertical coupling or electronic read-out through at least a photodetectors on the photonic sensor chip 116. The optical read-out and the electronic read-out are described further above. Arrows 220 shows a flow of at least a fluid 104 with one or more analytes 108. In some embodiments, one or more resonators 140 may include a binding ligand 224. At least a light source 128 in a reader device 132 may be tuned across the resonances of the sensor elements of the photonic sensor chip 116. A microfluidic channel of a microfluidic assembly 120 may be employed to flow the to-be-sensed one or more analytes 108 on the one or more micro-ring resonators 200. The refractive index change resulting from the presence of the one or more analytes on the surface of the one or more micro-ring resonators 200 may result in a shift in the resonance wavelength that can be detected by the reader device 132 as shown in FIG. 2C. The resulting wavelength shift may scale with the components (e.g. biomarkers) and concentration of the one or more analytes 108 and may be extracted from the photodetector outputs.

Figure 3:
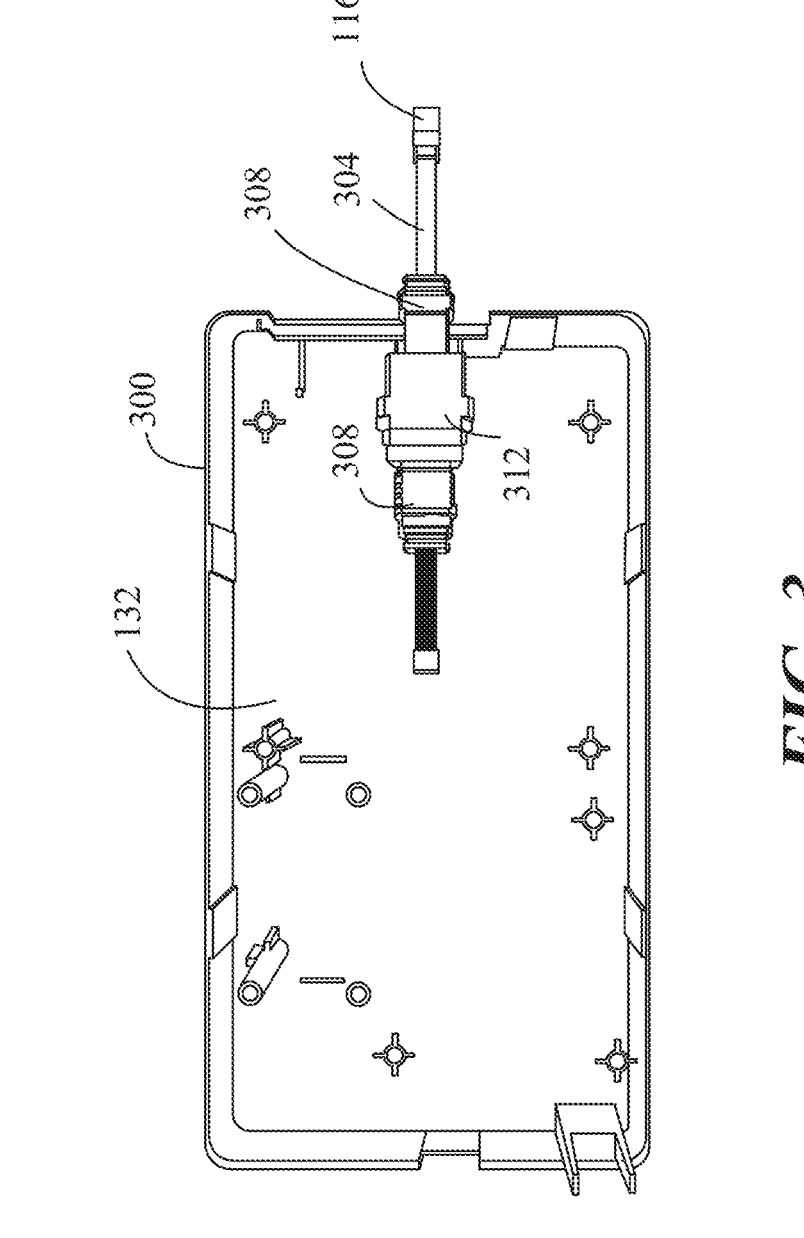
FIG. 3 is an exemplary embodiment of an apparatus for photonic biosensors for multiplexed diagnostics.

Referring now to FIG. 3, an exemplary embodiment of an apparatus 100 for photonic biosensors for multiplexed diagnostics is illustrated. Apparatus 100 includes a reader device 132. In some embodiments, the reader device 132 may include a housing 300 as described above. Apparatus 100 includes a photonic sensor chip 116. In some embodiments, the apparatus 100 may include a ribbon cable 304. In some embodiments, the apparatus 100 may include an MPO connector 308. In some embodiments, the apparatus 100 may include a plurality of MPO connectors 308. In some embodiments, the apparatus 100 may include an MPO adapter 312. The MPO connector 308 and/or the MPO adapter 312 may be any other connectors disclosed in the entirety of this disclosure. As a non-limiting example, the photonic sensor chip 116 may be optically coupled to a fiber array which is connected to a female mechanical transfer (MT) ferrule inside a multiple fiber push-on (MPO) connector 308. As another non-limiting example, the photonic sensor chip 116 may interrogate with the reader device 132 that provides an optical input signal to the photonic sensor chip 116 using an MPO adapter 312 while reading out of all the sensor elements on the photonic sensor chip 116.

Referring now to FIG. 4, an exemplary embodiment of a photonic sensor chip 116 of a portion of an apparatus 100 for photonic biosensors for multiplexed diagnostics. FIG. 4 illustrates optical interrogation of a photonic sensor chip 116 into a reader device 132 that facilitates at least a light source 128 and detection using edge coupling through an MPO connector 308 and a ribbon cable 304. In some embodiments, the photonic sensor chip 116 may include a combination of various photonic resonant structures such as but not limited to micro-ring resonators 200, photonic crystal cavities, grating structures, or interferometric structures such as Mach-Zehnder or Michelson interferometers, and the like. The laser input into and outputs from photonic sensor chip 116 may be coupled using edge coupling or grating coupler approaches, depending on the operating wavelength, propagation loss, power, and design constraints of the system. In some embodiments, the photonic sensor chip 116 may include 15 micro-ring resonators 200 as sensing elements. A fiber array coupling into the photonic sensor chip 116 may include one polarization-maintaining (PM) fiber 400 for optical input such as but not limited to an input optical signal 212 into the photonic sensor chip 116. A splitter network 136 on the photonic sensor chip 116 may divide the incoming light such as but not limited to the input optical signal 212 through the sensing elements and directed into 15 multi-mode fibers 404 on the fiber array back into the reader device 132 for processing.

With continued reference to FIG. 4, a photonic sensor chip configuration described herein, as shown in FIG. 2A-C-4, may be realized in a photonic platform and a waveguide configuration that suits requirements of sensitivity, power, multiplexity, and/or surface compatibility with a biochemistry. These material choices may include but are not limited to silicon, silica, and silicon nitride. Depending on the choice of the material and the waveguide configuration of the sensing element of the photonic sensor chip 116, the optical interface between the photonic sensor chip 116 and a reader device 132 may have to be optimized using design of low-loss spot size converters for edge-coupling configuration and low-loss, low-reflection, broadband grating couplers for vertical coupling configurations.

With continued reference to FIG. 4, a laser input into a photonic sensor chip 116 may be split across an array of sensing elements and may be read-out simultaneously allowing parallel sensing of a variety of one or more analytes 108. A splitter network 136 depicted may be realized using any number of coupling systems (e.g. binary tree of directional couplers, multi-mode-interference couplers, etc.) A required flatness of a splitting ratio across the tuning range of at least a light source 128 may be determined by thermal or non-linear effects of one or more resonators 140 or other sensor elements employed for the application. Improved compactness of the splitter network 136 may also be realized through implementation of a series of 1×N splitters comprising any number of coupling systems and/or coupler configurations including those described above. The splitter network 136 can take any form and can also be a combination of switches, wavelength multiplexing and so on.

Figure 5:
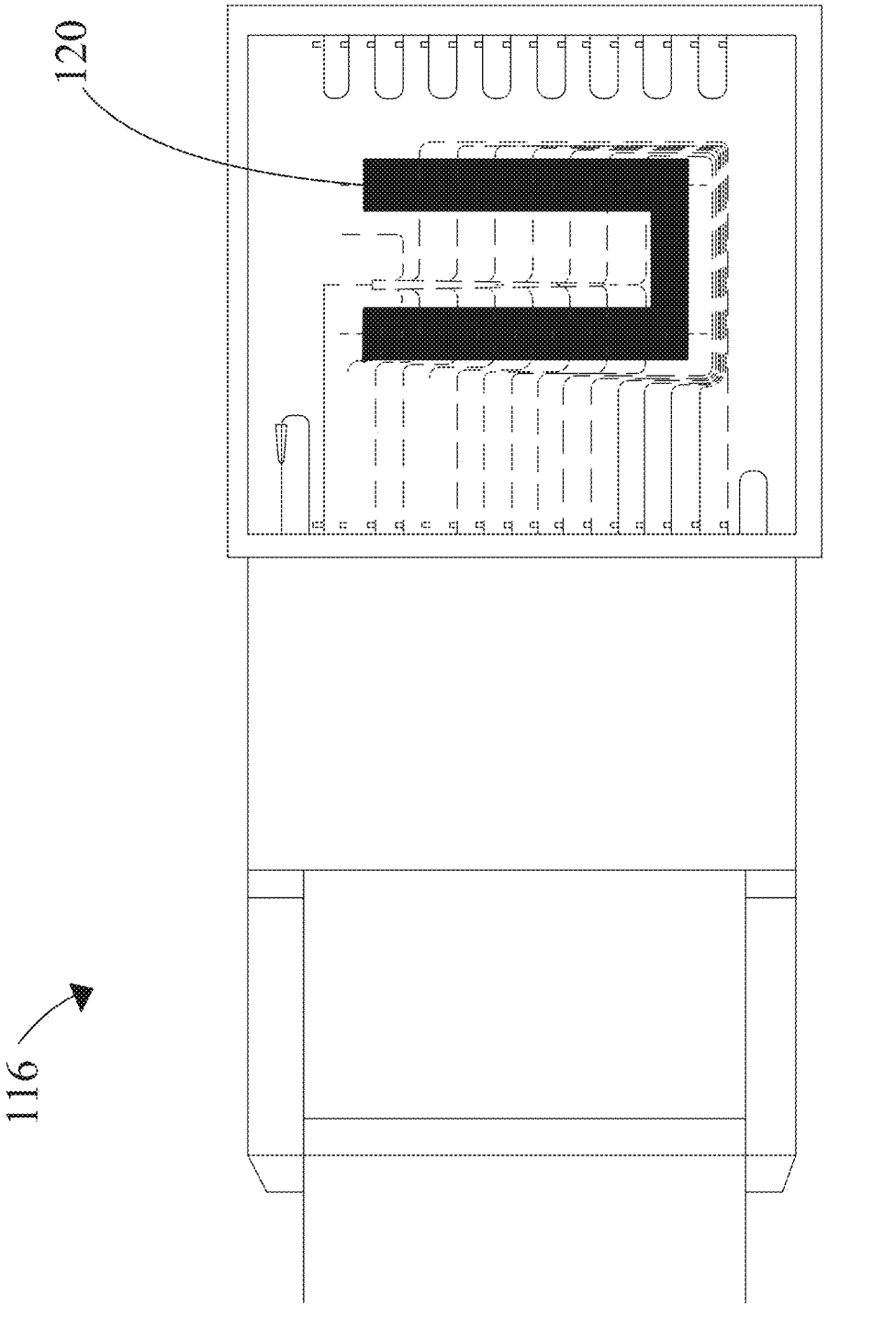
FIG. 5 is an exemplary embodiment of a layout of a microfluidic assembly.

Referring now to FIG. 5, an exemplary embodiment of a layout of a microfluidic assembly 120 lying atop sensing elements of a photonic sensor chip 116 is illustrated. FIG. 5 shows an example layout of a gasket designed to create a microfluidic path atop the sensing elements on the photonic chip surface of photonic sensor chip 116. The surface of the photonic sensor chip 116 may be functionalized with at least a fluid 104 with one or more analytes 108 of interest, for instance, with an antibody to detect the associated antigen expected in the biological fluidic sample to be flowed. In the current embodiment depicted in FIG. 2A-2C— FIG. 4, in addition to an optical input and readout, a reader device 132 may provide a miniaturized microfluidic pump mechanism that achieves routing of the at least a fluid 104 through the surface of the photonic sensor chip 116 through push/pull actions on a plunger available in a disposable microfluidic cartridge containing the photonic sensor chip 116.

Figure 6B:
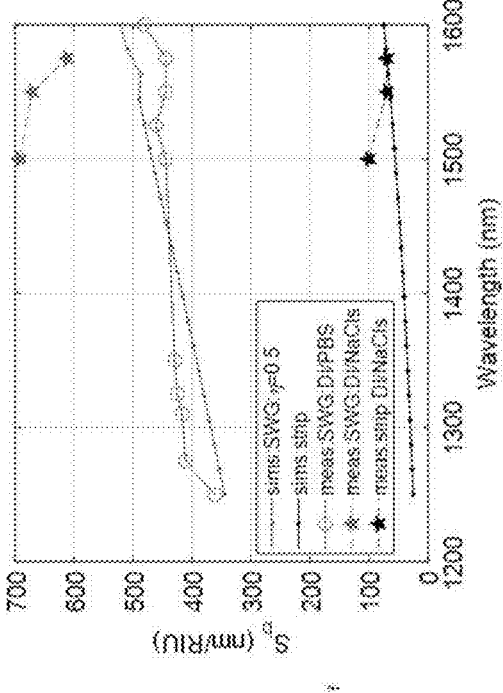
FIG. 6B is an exemplary waveguide schematic of a silicon sub-wavelength grating resonators on a silicon-on-insulator wafer.
Figure 6A:
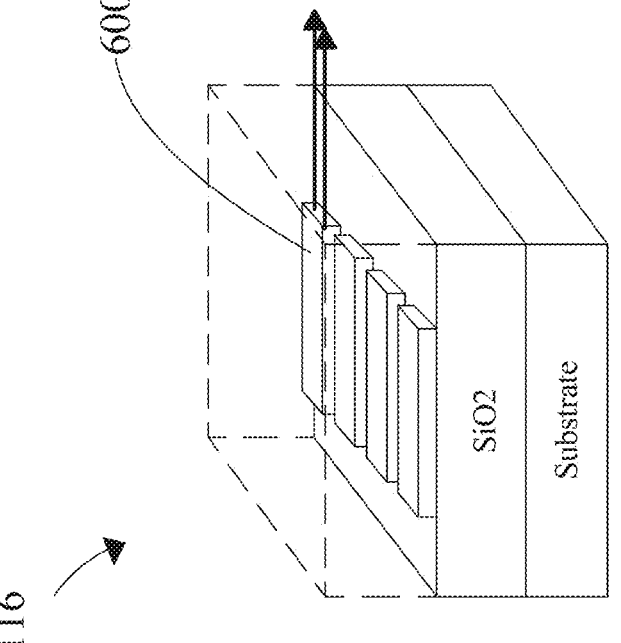
FIG. 6A is an exemplary embodiment of a cross section of a portion of a photonic sensor chip with a silicon sub-wavelength grating resonators.

Referring now to FIG. 6A-B, FIG. 6A illustrates an exemplary embodiment of a cross section of a portion of a photonic sensor chip 116. In some embodiments, the photonic sensor chip 116 may include sub-wavelength silicon grating resonators 600 with a duty cycle of 50% that were analyzed for their bulk refractive index sensitivity>350 nm/RIU in both O-band and C-band operations. FIG. 6B illustrates a waveguide schematic of the silicon sub-wavelength grating (SWG) resonators 600 with a grating period A, effective index $n_{eff}$, and a duty cycle η, realized on a silicon-on-insulator (SOI) wafer that shows example simulated and empirical results of bulk sensitivity for the silicon SWG resonators 600 with a thickness of 220 nm, width of 470 nm, grating period of 250 nm, and 50% duty cycle operating in O (1260 nm-1360 nm) and C+L wavelength bands (1530 nm-1565 nm+1565 nm-1625 nm).

Figure 7B:
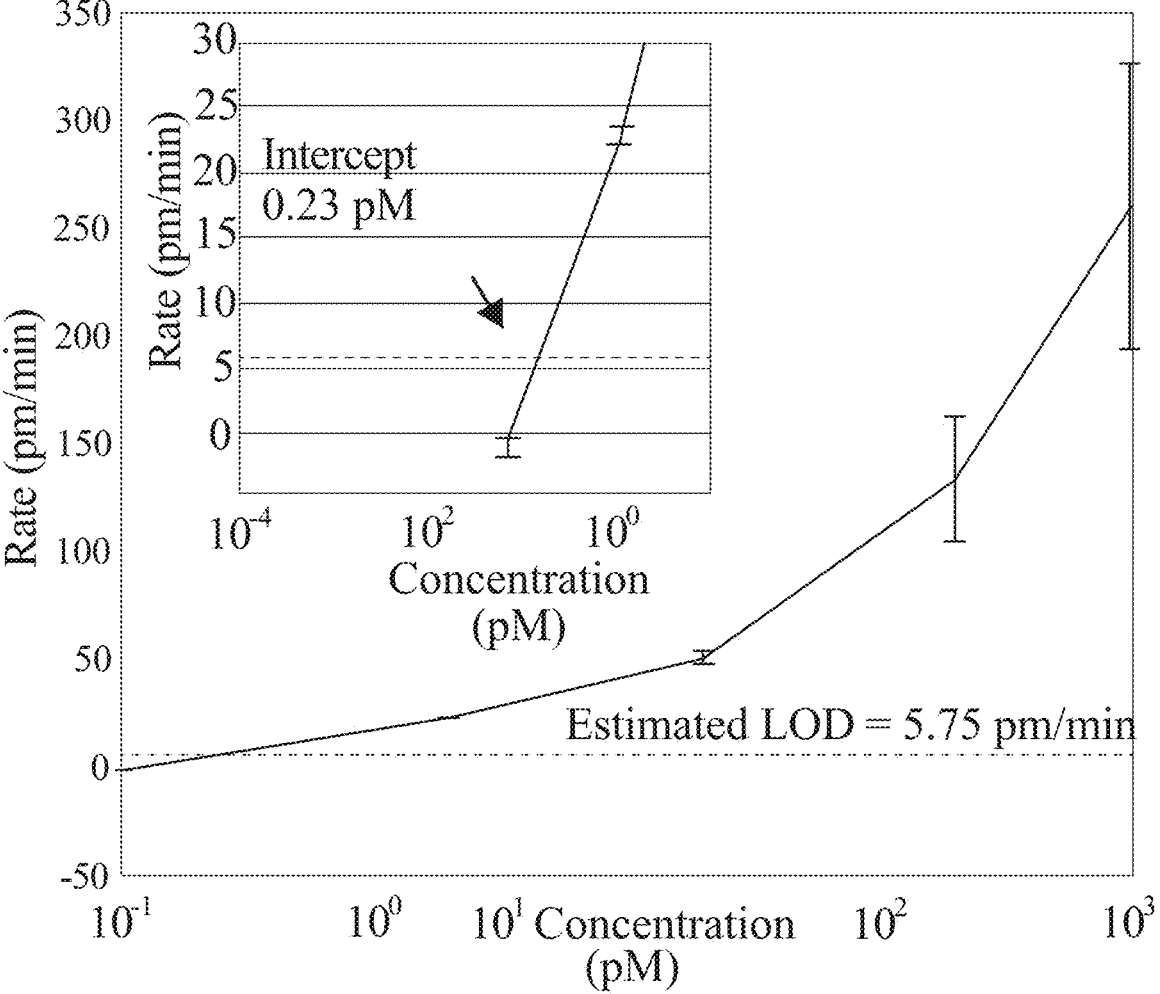
FIG. 7B shows an empirical result of SARS-COV-2 protein detected in a pooled nasal swab using silicon sub-wavelength grating resonators.

Referring now to FIG. 7A-B, FIG. 7B shows empirical results of SARS-COV-2 protein detected in a pooled nasal swab using silicon SWG resonators 600 operating in C-band wavelength regime. The empirical detection results of SARS-COV-2 N-protein detection down to 0.23 pM was successfully measured in a limit of detection experiment that resulted in a wavelength shift rate as low as 5.75 pm/min. FIG. 7A shows these measurements in addition to the detailed concentration curve that shows increased standard deviations for higher concentrations. The measured limit of detection (LOD) is nearly 0.23 pM of protein concentration which resulted in a resonance wavelength shift rate of ~5.75 pm/min.

Figures 8A, 8B:
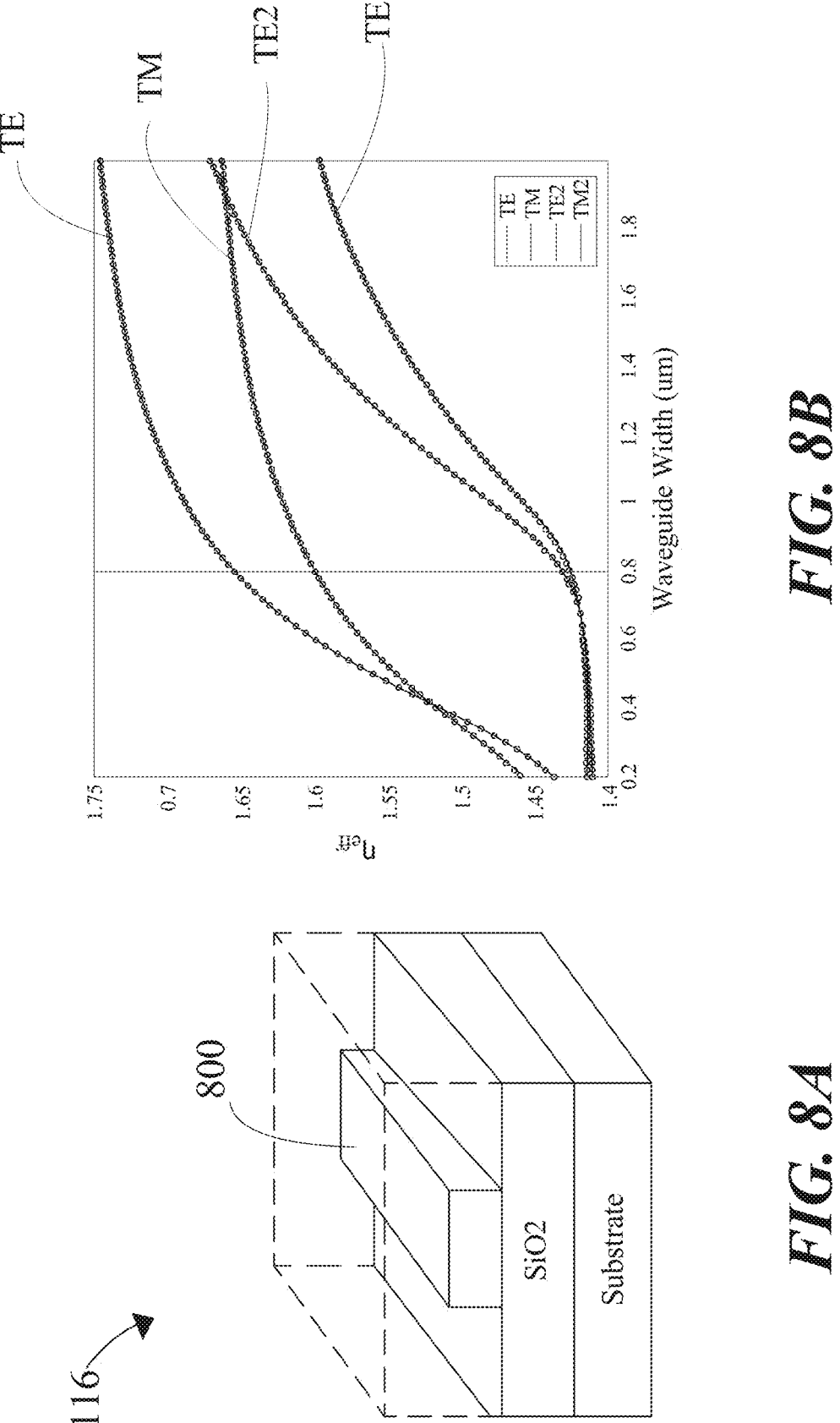
FIG. 8A is an exemplary embodiment of a cross section of a portion of a photonic sensor chip with a silicon nitride ($Si_3N_4$) strip waveguide micro-ring resonator.
FIG. 8B shows design parameters for strip silicon nitride waveguide resonators to be used for multiplexed sensing.

Referring now to FIG. 8A-B, FIG. 8A shows the example waveguide geometry, effective mode analysis, and directional coupler simulations of a silicon nitride ($Si_3N_4$) strip waveguide micro-ring resonator 800 with aqueous solution cladding operating in O-band wavelength range. FIG. 8B describes a choice of design parameters for strip silicon nitride waveguide resonators 800 to be used for multiplexed sensing operating in O-band. In this example, the nominal waveguide width was chosen to be 800 nm to operate in single-TE mode at 1310 nm, while still maintaining low-loss and bending radius.

Figure 9B:
FIG. 9B shows empirical results of SARS-COV-2 protein detected using a disposable microfluidic cartridge interrogated using a reader device.

Referring now to FIG. 9A-B, as shown in FIG. 9A, a waveguide configuration of a silicon nitride strip waveguide resonators 800 used in a proposed photonic sensor chip 116 may comprise one or more of the several periodic and/or interferometric structures, including but not limited to, periodic gratings, sub-wavelength gratings, slot waveguides, strip waveguides, strip waveguides with adiabatically varying width, or any combination of these structures and geometries, that operate in a polarization mode configuration of choice, depending on the required sensitivity and limit of detection. FIG. 9B shows the empirical results of SARS-COV-2 protein detected in a pooled nasal swab and CRP protein in filtered blood measured using a disposable microfluidic cartridge interrogated via the reader device 132. Both these detection schemes used custom developed assays and positive/negative controls for analyte detection. FIG. 9B shows the multiplexed empirical detection of SARS-COV-2 protein in a pooled nasal swab and CRP protein in filtered blood using positive and negative controls, detected using the silicon nitride strip waveguide resonators 800 on the photonic sensor chip 116 operating in O-band wavelength regime.

Figure 10B:
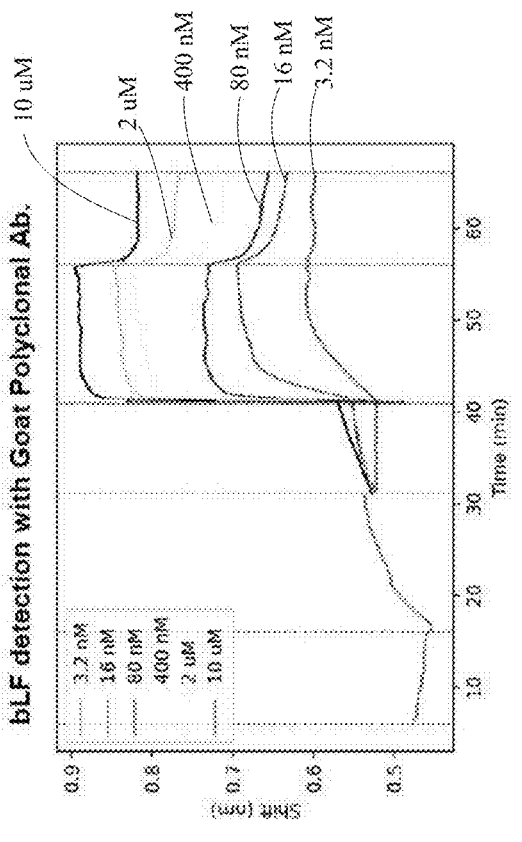
FIG. 10B shows empirical determination of real-time binding kinetics of bLF.
Figure 10A:
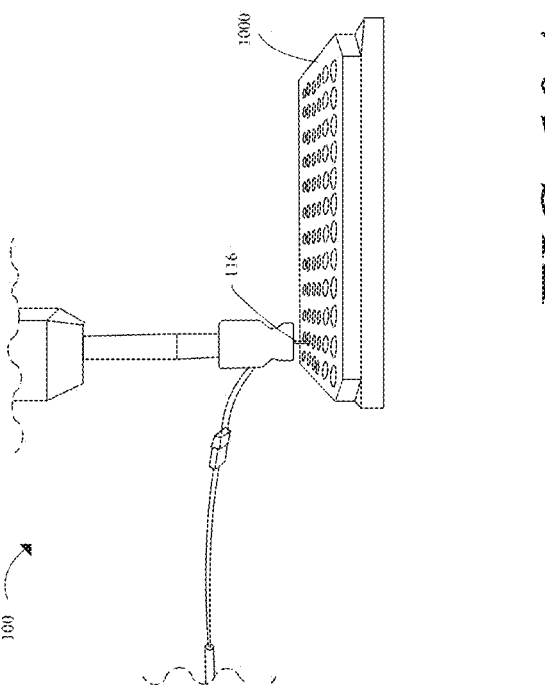
FIG. 10A is an exemplary embodiment of a portion of an apparatus with a photonic sensor chip dipped in a well-plate.

Referring now to FIG. 10A-B, FIG. 10A illustrates a portion of an apparatus 100 with a photonic sensor chip 116 dipped in a well-plate 1000. In some cases, an interaction of a functionalized chip surface with biological analytes 108 of interest may be achieved through dipping of the photonic sensor chip 116 into the well-plate 1000, as shown in FIG. 10A, while retaining the optical interrogation interface with a reader device 132. Dipping of the photonic sensor chip 116 into the liquid (at least a fluid 104) offers a flexible method to investigate real-time binding dynamics of multiple analytes 108 of interest, making the technique friendly for research and development of pharmacokinetics and biology. FIG. 10B shows empirical determination of real-time binding kinetics of bLF with goat polyclonal antibodies when the silicon nitride chip 800 was dipped into the well plate 1000 with the analyte 108.

Figure 11:
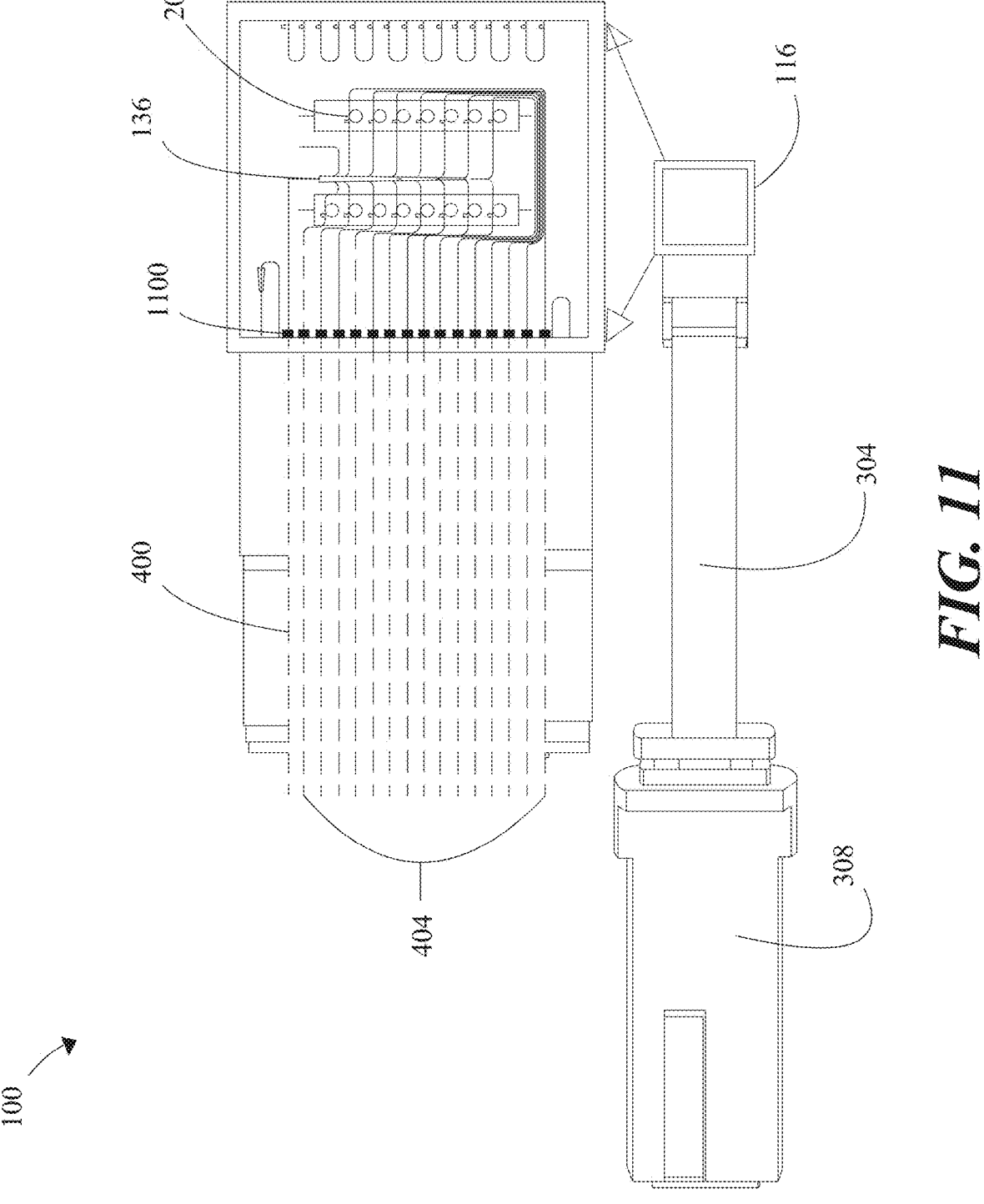
FIG. 11 is an exemplary embodiment of a portion of an apparatus with a photonic sensor chip with on-chip photo-detectors.

Referring now to FIG. 11, FIG. 11 illustrates an exemplary embodiment of a photonic sensor chip 116 with on-chip photodetectors 1100 to enable electrical readout. In some cases, the photodetectors 1100 for the electrical readout can be directly placed on the photonic sensor chip 116 through flip-chip bonding or other attachment approaches as shown in FIG. 11. In this case, an optical interrogation of sensing elements on the photonic sensor chip 116 may be limited only to a laser input into the photonic sensor chip 116 while optical readouts may be replaced by an electrical interface between a reader device 132 and a cartridge housing the photonic sensor chip 116. In some cases, a fluidic routing of the biological sample (the at least a fluid 104) on the photonic sensor chip 116 can be achieved through passive microfluidic approaches employing capillary action in the fluidic channels. In such cases, the photonic interrogation of the reader device 132 may only be limited to optical and/or electrical readout without the need for fluidic routing through an active pump. The choice of an optical source (at least a light source 128) may be determined by the required wavelength resolution for sensing (e.g., 830 nm, 980 nm, 1064 nm, 1310 nm, 1550 nm or other visual/mid-IR ranges), the material platform of the passive components, and/or the sampling rate of the read-out electronics. The frequency drift of the laser caused by the inherent white and flicker frequency noise components may lower the achievable wavelength resolution in the sampling period while the required relative-intensity-noise and the output power of the laser may be determined by the dynamic range of the electronics and the extinction ratio of the sensor element.

Referring now to FIG. 12, an exemplary flow diagram of a method 1200 of use of photonic biosensors for multiplexed diagnostics. Method 1200 includes step 1205 of obtaining at least a fluid, wherein the at least a fluid comprises one or more analytes. These may be implemented as disclosed with respect to FIG. 1-11.

With continued reference to FIG. 12, a method 1200 includes a step 1210 of substantially contacting at least a fluid and one or more resonators of a photonic sensor chip of a portable device, wherein the portable device is configured for point-of-care diagnostics. In some embodiments, the photonic sensor chip may further include a splitter network, wherein the splitter network may be configured to divide an input optical signal into two or more output optical signals. In some embodiments, the one or more resonators may be coupled with an optical waveguide, wherein the optical waveguide may be configured to receive the two or more output optical signals from the splitter network and output an optical output to at least a photodetector. In some embodiments, the photonic sensor chip may further include the at least a photodetector. In some embodiments, the photonic sensor chip may further include a microfluidic assembly, wherein the microfluidic assembly may include a microfluidic pump, wherein the microfluidic pump may be configured to route a flow of the at least a fluid and at least a reservoir, wherein the at least a reservoir may be configured to contain the at least a fluid. In some embodiments, the microfluidic assembly may be atop the one or more resonators of the photonic sensor chip. These may be implemented as disclosed with respect to FIG. 1-11.

With continued reference to FIG. 12, a method 1200 includes a step 1215 of providing, using at least a light source of a reader device of a portable device communicatively connected to a photonic sensor chip of a portable device using a connecting system, an input optical signal to the photonic sensor chip. In some embodiments, the connecting system may further include a fiber array comprising an optical fiber, wherein the fiber array may include a polarization-maintaining optical fiber (PM fiber), wherein the PM fiber may be configured to transmit an input optical signal into the photonic sensor chip and a plurality of multi-mode fibers, wherein the plurality of multi-mode fibers may be configured to transmit an optical output into the reader device. In some embodiments, the connecting system may include a wavelength-division multiplexing (WDM) system. In some embodiments, the connecting system may further include a multi-fiber push-on (MPO) connector. These may be implemented as disclosed with respect to FIG. 1-11.

With continued reference to FIG. 12, method 1200 includes step 1220 of receiving, using a reader device, one or more sensor signals from a photonic sensor chip. In some embodiments, method 1200 may further include receiving, using the reader device, one or more sensor signals from an optical waveguide using a vertical coupling of an optical fiber. These may be implemented as disclosed with respect to FIG. 1-11.

With continued reference to FIG. 12, method 1200 includes step 1225 of determining, using a reader device, one or more characteristics of one or more analytes of at least a fluid as a function of one or more sensor signals. These may be implemented as disclosed with respect to FIG. 1-11.

The description herein is provided with the intention to enable a person having ordinary skill in the art to make use of the disclosure. The description herein, with connection to the drawings, describes example configurations and does not represent all the examples that may be implemented or that are within the scope of the present disclosure. Various modifications to the details provided within the disclosure will be apparent to a person having ordinary skill in the art, and the general principles outlined herein may be applied to other variations without departing from the scope of the disclosure. The term "example" means "serving as an example, illustration, or instance" and not "preferred over other examples."

The specific details in the detailed description included are provided for the purpose of providing an understanding of the described techniques. These techniques, however, may be practiced with or without these specific details. In some cases, known structures and devices are presented in broad detail to avoid obscuring the concepts of the described examples. Thus, the disclosure is not limited to the examples and designs described herein but is to be conferred the broadest scope consistent with the principles and novel features disclosed herein.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 13:
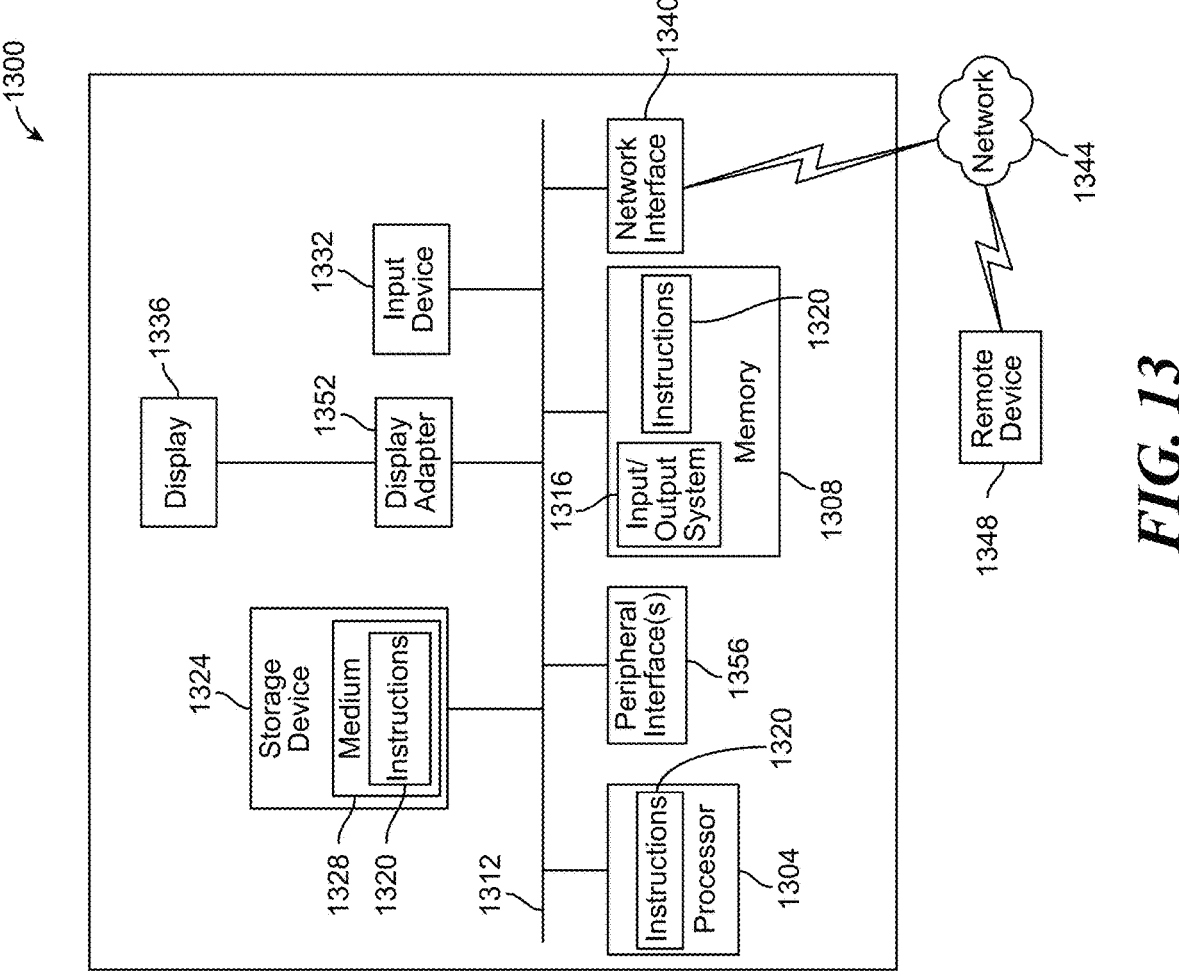
FIG. 13 is a block diagram of a computing system that can be used to implement any one or more of the methodologies disclosed herein and any one or more portions thereof.

FIG. 13 shows a diagrammatic representation of one embodiment of a computing device in the exemplary form of a computer system 1300 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1300 includes a processor 1304 and a memory 1308 that communicate with each other, and with other components, via a bus 1312. Bus 1312 may include any of several types of bus structures including, but not limited to, a memory bus, a memory controller, a peripheral bus, a local bus, and any combinations thereof, using any of a variety of bus architectures.

Processor 1304 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1304 may be organized according to Von Neumann and/or Harvard architecture as a non-limiting example. Processor 1304 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), a System on Module (SOM), and/or system on a chip (SoC).

Memory 1308 may include various components (e.g., machine-readable media) including, but not limited to, a random-access memory component, a read only component, and any combinations thereof. In one example, a basic input/output system 1316 (BIOS), including basic routines that help to transfer information between elements within computer system 1300, such as during start-up, may be stored in memory 1308. Memory 1308 may also include (e.g., stored on one or more machine-readable media) instructions (e.g., software) 1320 embodying any one or more of the aspects and/or methodologies of the present disclosure. In another example, memory 1308 may further include any number of program modules including, but not limited to, an operating system, one or more application programs, other program modules, program data, and any combinations thereof.

Computer system 1300 may also include a storage device 1324. Examples of a storage device (e.g., storage device 1324) include, but are not limited to, a hard disk drive, a magnetic disk drive, an optical disc drive in combination with an optical medium, a solid-state memory device, and any combinations thereof. Storage device 1324 may be connected to bus 1312 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1324 (or one or more components thereof) may be removably interfaced with computer system 1300 (e.g., via an external port connector (not shown)). Particularly, storage device 1324 and an associated machine-readable medium 1328 may provide nonvolatile and/or volatile storage of machine-readable instructions, data structures, program modules, and/or other data for computer system 1300. In one example, software 1320 may reside, completely or partially, within machine-readable medium 1328. In another example, software 1320 may reside, completely or partially, within processor 1304.

Computer system 1300 may also include an input device 1332. In one example, a user of computer system 1300 may enter commands and/or other information into computer system 1300 via input device 1332. Examples of an input device 1332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1332 may be interfaced to bus 1312 via any of a variety of interfaces (not shown) including, but not limited to, a serial interface, a parallel interface, a game port, a USB interface, a FIRE-WIRE interface, a direct interface to bus 1312, and any combinations thereof. Input device 1332 may include a touch screen interface that may be a part of or separate from display 1336, discussed further below. Input device 1332 may be utilized as a user selection device for selecting one or more graphical representations in a graphical interface as described above.

A user may also input commands and/or other information to computer system 1300 via storage device 1324 (e.g., a removable disk drive, a flash drive, etc.) and/or network interface device 1340. A network interface device, such as network interface device 1340, may be utilized for connecting computer system 1300 to one or more of a variety of networks, such as network 1344, and one or more remote devices 1348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1344, may employ a wired and/or a wireless mode of communication. In general, any network topology may be used. Information (e.g., data, software 1320, etc.) may be communicated to and/or from computer system 1300 via network interface device 1340.

Computer system 1300 may further include a video display adapter 1352 for communicating a displayable image to a display device, such as display device 1336. Examples of a display device include, but are not limited to, a liquid crystal display (LCD), a cathode ray tube (CRT), a plasma display, a light emitting diode (LED) display, and any combinations thereof. Display adapter 1352 and display device 1336 may be utilized in combination with processor 1304 to provide graphical representations of aspects of the present disclosure. In addition to a display device, computer system 1300 may include one or more other peripheral output devices including, but not limited to, an audio speaker, a printer, and any combinations thereof. Such peripheral output devices may be connected to bus 1312 via a peripheral interface 1356. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve apparatuses and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for photonic biosensors for multiplexed diagnostics, wherein the apparatus comprises:
   a portable device configured for point-of-care diagnostics, wherein the portable device comprises:
   a disposable microfluidic cartridge, the disposable microfluidic cartridge comprising a photonic sensor chip, the photonic sensor chip comprising:
   one or more resonators, wherein the one or more resonators is substantially in contact with at least a fluid, wherein the at least a fluid comprises one or more analytes, wherein the one or more resonators comprises a plurality of ring resonators, wherein a gap exists between the plurality of ring resonators and an optical waveguide, wherein the plurality of ring resonators comprises:
   a first ring resonator configured to detect a first analyte of the one or more analytes of the at least a fluid; and a second ring resonator configured to detect a second analyte of the one or more analytes of the at least a fluid, wherein the second analyte is different from the first analyte; and a microfluidic assembly situated atop the one or more resonators and located along a surface of the photonic sensor chip;

a reader device communicatively connected to the photonic sensor chip, wherein:

the reader device comprises at least a light source; and the reader device is configured to:

provide an input optical signal using the at least a light source;

receive one or more sensor signals from the photonic sensor chip; and determine one or more characteristics of the first analyte and the second analyte of the one or more analytes of the at least a fluid as a function of the one or more sensor signals provided by the photonic sensor chip including the first ring resonator and the second ring resonator; and a connecting system, wherein the connecting system is configured to connect the photonic sensor chip and the reader device, and wherein the connecting system further comprises a multi-fiber push-on (MPO) connector.

2. The apparatus of claim 1, wherein the photonic sensor chip further comprises a splitter network, wherein the splitter network is configured to divide the input optical signal into two or more output optical signals.

3. The apparatus of claim 2, wherein the one or more resonators is coupled with the optical waveguide, wherein the optical waveguide is configured to:

receive the two or more output optical signals from the splitter network; and output an optical output to at least a photodetector.

4. The apparatus of claim 3, wherein the reader device is further configured to receive the one or more sensor signals from the optical waveguide using a vertical coupling of an optical fiber.

5. The apparatus of claim 4, wherein the connecting system further comprises a fiber array comprising the optical fiber, wherein the fiber array comprises:

a polarization-maintaining optical fiber (PM fiber), wherein the PM fiber is configured to transmit the input optical signal into the photonic sensor chip; and a plurality of multi-mode fibers, wherein the plurality of multi-mode fibers is configured to transmit the optical output into the reader device.

6. The apparatus of claim 1, wherein the connecting system comprises a wavelength-division multiplexing (WDM) system.

7. The apparatus of claim 1, wherein the microfluidic assembly comprises:

a microfluidic pump, wherein the microfluidic pump is configured to route a flow of the at least a fluid; and at least a reservoir, wherein the at least a reservoir is configured to contain the at least a fluid.

8. The apparatus of claim 7, wherein the microfluidic assembly is atop the one or more resonators of the photonic sensor chip.

9. The apparatus of claim 1, wherein the connecting system further comprises a ribbon cable, and wherein the ribbon cable is configured to connect the MPO connector and the photonic sensor chip to the reader device.

10. The apparatus of claim 1, wherein the connecting system further comprises:

a fiber array optically connected to the photonic sensor chip and connected to a female mechanical transfer module ferrule inside a first MPO connector;

the first MPO connector connecting the fiber array to an MPO adapter; and a second MPO connector connecting the reader device to the MPO adapter, wherein the photonic sensor chip is configured to interrogate with the reader device through the connecting system.

11. A method of use of photonic biosensors for multiplexed diagnostics, the method comprising:

obtaining a portable device comprising a disposable microfluidic cartridge, wherein the disposable microfluidic cartridge comprises at least a fluid, wherein the at least a fluid comprises one or more analytes and wherein the disposable microfluidic cartridge comprises:

a photonic sensor chip, the photonic sensor chip comprising:

one or more resonators substantially in contact with the at least a fluid, wherein the portable device is configured for point-of-care diagnostics, wherein the one or more resonators comprises a plurality of ring resonators, wherein a gap exists between the plurality of ring resonators and an optical waveguide; and a microfluidic assembly situated atop the one or more resonators and located along a surface of the photonic sensor chip;

detecting, using a first ring resonator of the plurality of ring resonators, a first analyte of the one or more analytes of the at least a fluid;

detecting, using a second ring resonator of the plurality of ring resonators, a second analyte of the one or more analytes of the at least a fluid, wherein the second analyte is different from the first analyte;

providing, using at least a light source of a reader device of the portable device communicatively connected to the photonic sensor chip, an input optical signal to the photonic sensor chip;

providing a connecting system to connect the photonic sensor chip and the reader device, wherein the connecting system comprises a multi-fiber push-on (MPO) connector;

receiving, using the reader device, one or more sensor signals from the photonic sensor chip; and determining, using the reader device, one or more characteristics of the first analyte and the second analyte of the one or more analytes of the at least a fluid as a function of the one or more sensor signals provided by the photonic sensor chip including the first ring resonator and the second ring resonator.

12. The method of claim 11, wherein the photonic sensor chip further comprises a splitter network, wherein the splitter network is configured to divide the input optical signal into two or more output optical signals.

13. The method of claim 12, wherein the one or more resonators is coupled with the optical waveguide, wherein the optical waveguide is configured to:

receive the two or more output optical signals from the splitter network; and output an optical output to at least a photodetector.

14. The method of claim 13, further comprising:

receiving, using the reader device, the one or more sensor signals from the optical waveguide using a vertical coupling of an optical fiber.

15. The method of claim 14, wherein the connecting system further comprises a fiber array comprising the optical fiber, wherein the fiber array comprises:

a polarization-maintaining optical fiber (PM fiber), wherein the PM fiber is configured to transmit the input optical signal into the photonic sensor chip; and a plurality of multi-mode fibers, wherein the plurality of multi-mode fibers is configured to transmit the optical output into the reader device.

16. The method of claim 11, wherein the connecting system comprises a wavelength-division multiplexing (WDM) system.

17. The method of claim 11, wherein the microfluidic assembly comprises:

a microfluidic pump, wherein the microfluidic pump is configured to route a flow of the at least a fluid; and at least a reservoir, wherein the at least a reservoir is configured to contain the at least a fluid.

18. The method of claim 17, wherein the microfluidic assembly is atop the one or more resonators of the photonic sensor chip.

19. The method of claim 11, wherein the connecting system further comprises a ribbon cable, and wherein the ribbon cable is configured to connect the MPO connector and the photonic sensor chip to the reader device.

20. The method of claim 11, wherein the connecting system further comprises:

a fiber array optically connected to the photonic sensor chip and connected to a female mechanical transfer module ferrule inside a first MPO connector;

the first MPO connector connecting the fiber array to an MPO adapter; and a second MPO connector connecting the reader device to the MPO adapter, wherein the photonic sensor chip is configured to interrogate with the reader device through the connecting system.

* * * * *